United States Patent
Greenberg et al.

(10) Patent No.: US 11,912,734 B2
(45) Date of Patent: Feb. 27, 2024

(54) SOLID-PHASE SYNTHESIS OF OLIGONUCLEOTIDES CONTAINING N6-(2-DEOXY-ALPHA,BETA-DERYTH-ROPENTOFURANOSYL)-2,6-DIAMINO-4-HYDROXY-5-FORMAMIDOPYRIMIDINE (FAPY•DG)

(71) Applicant: The Johns Hopkins University, Baltimore, MD (US)

(72) Inventors: Marc M. Greenberg, Baltimore, MD (US); Haozhe Yang, Baltimore, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 131 days.

(21) Appl. No.: 17/161,272

(22) Filed: Jan. 28, 2021

(65) Prior Publication Data
US 2021/0238213 A1     Aug. 5, 2021

Related U.S. Application Data

(60) Provisional application No. 62/966,655, filed on Jan. 28, 2020.

(51) Int. Cl.
    *C07H 1/00*             (2006.01)
    *C07H 19/06*           (2006.01)
    *C07H 21/00*           (2006.01)

(52) U.S. Cl.
    CPC ............ *C07H 1/00* (2013.01); *C07H 19/06* (2013.01); *C07H 21/00* (2013.01)

(58) Field of Classification Search
CPC .......... C07H 21/00; C07H 21/04; C07H 1/00; C07H 19/06
See application file for complete search history.

(56) References Cited

PUBLICATIONS

Beier et al., Journal of Biotechnology, 2002, 94, p. 15-22. (Year: 2002).*
Weiler et al., Anal. Biochem., 1996, 243, p. 218-227. (Year: 1996).*
Haraguchi et al., J. Am. Chem. Soc., 2001, 123, 8636-8637. (Year: 2001).*
Allgayer et al., Widespread transcriptional gene inactivation initiated by a repair intermediate of 8-oxoguanine. Nucleic Acids Res. Sep. 6, 2016;44(15):7267-80.
Alshykhly et al., 5-Carboxamido-5-formamido-2-iminohydantoin, in Addition to 8-oxo-7,8-Dihydroguanine, Is the Major Product of the Iron-Fenton or X-ray Radiation-Induced Oxidation of Guanine under Aerobic Reducing Conditions in Nucleoside and DNA Contexts. J Org Chem. Jul. 17, 2015;80(14):6996-7007.
Amente et al., Genome-wide mapping of 8-oxo-7,8-dihydro-2'-deoxyguanosine reveals accumulation of oxidatively-generated damage at DNA replication origins within transcribed long genes of mammalian cells. Nucleic Acids Res. Jan. 10, 2019;47(1):221-236.
Babaoglu et al., Crystal structure of 7,8-dihydropteroate synthase from Bacillus anthracis: mechanism and novel inhibitor design. Structure. Sep. 2004;12(9):1705-17.
Bag et al., Triazolyl donor/acceptor chromophore decorated unnatural nucleosides and oligonucleotides with duplex stability comparable to that of a natural adenine/thymine pair. J Org Chem. Jan. 18, 2013;78(2):278-91.
Becker et al., A high-yielding, strictly regioselective prebiotic purine nucleoside formation pathway. Science. May 13, 2016;352(6287):833-6.
Berger et al., Isolation and Characterization of the Radiation-Induced Degradation Products of 2'-Deoxyguanosine in Oxygen-Free Solutions. Z. Naturforsch., 1985. 40b, 1519-1531.
Bergeron et al., HO* radicals induce an unexpected high proportion of tandem base lesions refractory to repair by DNA glycosylases. Proc Natl Acad Sci U S A. Mar. 23, 2010;107(12):5528-33.
Burgdorf et al., Synthesis, stability, and conformation of the formamidopyrimidine G DNA lesion. Chemistry. Jan. 4, 2002;8(1):293-301.
Cadet et al., DNA base damage by reactive oxygen species, oxidizing agents, and UV radiation. Cold Spring Harb Perspect Biol. Feb. 1, 2013;5(2):a012559. 18 pages.
Cadet et al., Formation and repair of oxidatively generated damage in cellular DNA. Free Radic Biol Med. Jun. 2017;107:13-34.
Cai et al., Acylation of protein lysines by trichloroethylene oxide. Chem Res Toxicol. May 2000;13(5):327-35.
Chmiel et al., Insight into the functional consequences of inherited variants of the hMYH adenine glycosylase associated with colorectal cancer: complementation assays with hMYH variants and pre-steady-state kinetics of the corresponding mutated E.coli enzymes. J Mol Biol. Mar. 21, 2003;327(2):431-43.
Christov et al., Replication past the N5-methyl-formamidopyrimidine lesion of deoxyguanosine by DNA polymerases and an improved procedure for sequence analysis of in vitro bypass products by mass spectrometry. Chem Res Toxicol. Jun. 2009;22(6):1086-95.
Christov et al., Site-specific synthesis and characterization of oligonucleotides containing an N6-(2-deoxy-D-erythro-pentofuranosyl)-2,6-diamino-3,4-dihydro-4-oxo-5-N-methylformamidopyrimidine lesion, the ring-opened product from N7-methylation of deoxyguanosine. Chem Res Toxicol. Dec. 2008;21(12):2324-33.
Coste et al., Structural basis for the recognition of the FapydG lesion (2,6-diamino-4-hydroxy-5-formamidopyrimidine) by formamidopyrimidine-DNA glycosylase. J Biol Chem. Oct. 15, 2004;279(42):44074-83.
Delaney et al., Synthesis of oligonucleotides and thermal stability of duplexes containing the beta-C-nucleoside analogue of Fapy*dG. Chem Res Toxicol. Nov. 2002;15(11):1460-5.
Dizdaroglu et al., Formamidopyrimidines in DNA: mechanisms of formation, repair, and biological effects. Free Radic Biol Med. Dec. 15, 2008;45(12):1610-21.
Dizdaroglu. Oxidatively induced DNA damage and its repair in cancer. Mutat Res Rev Mutat Res. Jan.-Mar. 2015;763:212-45.

(Continued)

*Primary Examiner* — Jonathan S Lau
(74) *Attorney, Agent, or Firm* — Casimir Jones, SC; Jeffrey W. Childers

(57) ABSTRACT

A strategy using reverse phosphoramidites for synthesizing oligonucleotides containing Fapy·dG is disclosed.

24 Claims, 15 Drawing Sheets

Specification includes a Sequence Listing.

(56) References Cited

PUBLICATIONS

Douki et al., DNA tandem lesions containing 8-oxo-7,8-dihydroguanine and formamido residues arise from intramolecular addition of thymine peroxyl radical to guanine. Chem Res Toxicol. Mar. 2002;15(3):445-54.

Douki et al., Measurement of 2,6-diamino-4-hydroxy-5-formamidopyrimidine and 8-oxo-7,8-dihydroguanine in isolated DNA exposed to gamma radiation in aqueous solution. Carcinogenesis. Dec. 1997;18(12):2385-91.

Fleming et al., Oxidative DNA damage is epigenetic by regulating gene transcription via base excision repair. Proc Natl Acad Sci U S A. Mar. 7, 2017;114(10):2604-2609.

Freudenthal et al., Uncovering the polymerase-induced cytotoxicity of an oxidized nucleotide. Nature. Jan. 29, 2015;517(7536):635-9.

Gehrke et al., Unexpected non-Hoogsteen-based mutagenicity mechanism of FaPy-DNA lesions. Nat Chem Biol. Jul. 2013;9(7):455-61.

Greenberg. The formamidopyrimidines: purine lesions formed in competition with 8-oxopurines from oxidative stress. Acc Chem Res. Apr. 17, 2012;45(4):588-97.

Haraguchi et al., Synthesis and characterization of oligodeoxynucleotides containing formamidopyrimidine lesions and nonhydrolyzable analogues. J Am Chem Soc. Apr. 3, 2002;124(13):3263-9.

Haraguchi et al., Synthesis of oligonucleotides containing Fapy.dG (N6-(2-deoxy-alpha,beta-D-erythro-pentofuranosyl)-2,6-diamino-4-hydroxy-5-formamidopyrimidine). J Am Chem Soc. Sep. 5, 2001;123(35):8636-7.

Jaruga et al., Measurement of formamidopyrimidines in DNA. Free Radic Biol Med. Dec. 15, 2008;45(12):1601-9.

Jiang et al., Synthesis of oligonucleotides containing Fapy.dG (N(6)-(2-deoxy-alpha,beta-D-erythropentofuranosyl)-2,6-diamino-4-hydroxy-5-formamidopyrimidine) using a 5'-dimethoxytrityl dinucleotide phosphoramidite. J Org Chem. Jan. 7, 2005;70(1):141-9.

Kalam et al., Genetic effects of oxidative DNA damages: comparative mutagenesis of the imidazole ring-opened formamidopyrimidines (Fapy lesions) and 8-oxo-purines in simian kidney cells. Nucleic Acids Res. May 5, 2006;34(8):2305-15.

Kamimura et al., Synthesis of a dodecaribonucleotide, GUAUCAAUAAUG, by use of "fully" protected ribonucleotide building blocks. J. Am. Chem. Soc. 1984, 106(16), 4552-4557.

Krishnamurthy et al., Efficient removal of formamidopyrimidines by 8-oxoguanine glycosylases. Biochemistry. Jan. 22, 2008;47(3):1043-50.

Lukin et al., Novel post-synthetic generation, isomeric resolution, and characterization of Fapy-dG within oligodeoxynucleotides: differential anomeric impacts on DNA duplex properties. Nucleic Acids Res. Jul. 2011;39(13):5776-89.

McCulloch et al., The efficiency and fidelity of 8-oxo-guanine bypass by DNA polymerases delta and eta. Nucleic Acids Res. May 2009;37(9):2830-40.

Menoni et al., Base excision repair of 8-oxoG in dinucleosomes. Nucleic Acids Res. Jan. 2012;40(2):692-700.

Pan et al., Oxidized Guanine Base Lesions Function in 8-Oxoguanine DNA Glycosylase-1-mediated Epigenetic Regulation of Nuclear Factor KB-driven Gene Expression. J Biol Chem. Dec. 2, 2016;291(49):25553-25566.

Pande et al., Unlike catalyzing error-free bypass of 8-oxodGuo, DNA polymerase λ is responsible for a significant part of Fapy•dG-induced G → T mutations in human cells. Biochemistry. Mar. 17, 2015;54(10):1859-62.

Patro et al., Probing the configurations of formamidopyrimidine lesions Fapy.dA and Fapy.dG in DNA using endonuclease IV. Biochemistry. Oct. 26, 2004;43(42):13397-403.

Patro et al., Studies on the replication of the ring opened formamidopyrimidine, Fapy.dG in *Escherichia coli*. Biochemistry. Sep. 4, 2007;46(35):10202-12.

Porello et al., Single-turnover and pre-steady-state kinetics of the reaction of the adenine glycosylase MutY with mismatch-containing DNA substrates. Biochemistry. Oct. 20, 1998;37(42):14756-64.

Pouget et al., Formation of modified DNA bases in cells exposed either to gamma radiation or to high-LET particles. Radiat Res. May 2002;157(5):589-95.

Pratap et al., Direct conversion of aryl nitro compounds to formanilides under catalytic transfer hydrogenation conditions. Tetrahedron Lett., 2001, 42(10), 1983-1985.

Ravikumar et al., UnyLinker: An Efficient and Scaleable Synthesis of Oligonucleotides Utilizing a Universal Linker Molecule: A Novel Approach To Enhance the Purity of Drugs. Org. Process Res. Dev. 2008, 12, 3, 399-410.

Reddy et al., Fast cleavage and deprotection of oligonucleotides. Tetrahedron Lett. 1994, 35(25), 4311-4314.

Redstone et al., Oxidative Modification of the Potential G-Quadruplex Sequence in the PCNA Gene Promoter Can Turn on Transcription. Chem Res Toxicol. Mar. 18, 2019;32(3):437-446.

Robins et al., Nucleic Acid Related Compounds. 93. A Solution for the Historic Problem of Regioselective Sugar-Base Coupling To Produce 9-Glycosylguanines or 7-Glycosylguanines. J. Org. Chem. 1996, 61, 9207-9212.

Rolland et al., Convenient Preparation of 2-Deoxy-3,5-di-Op-toluoyl-α-D-erythro-pentofuranosyl Chloride. Syn. Comm. 1997, 27, 3505-3511.

Scaringe et al., Novel RNA Synthesis Method Using 5'-O-Silyl-2'-O-orthoester Protecting Groups. J. Am. Chem. Soc. 1998, 120, 11820-11821.

Schijf et al., Mixed carboxylic acid anhydrides VII. Synthesis of some mixed formic acid anhydrides. Recl. Trav. Chim. Pays-Bas, 1966, 85, 627-628.

Shafirovich et al., Removal of oxidatively generated DNA damage by overlapping repair pathways. Free Radic Biol Med. Jun. 2017;107:53-61.

The Glen Report. In Research, G. (ed.), Sterling, Virginia 20164. 2013. 12 pages.

Van der Kemp et al., PCNA monoubiquitylation and DNA polymerase eta ubiquitin-binding domain are required to prevent 8-oxoguanine-induced mutagenesis in *Saccharomyces cerevisiae*. Nucleic Acids Res. May 2009;37(8):2549-59.

Vlietstra et al., Trimethylacetic formic anhydride. Improved preparation and use as a highly efficient and selective N-formylating reagent. Recl. Trav. Chim. Pays-Bas, 1982, 101, 460-461.

Wei. Coupling activators for the oligonucleotide synthesis via phosphoramidite approach. Tetrahedron. 2013. 69 (18): 3615-3637.

Wiederholt et al., Repair of DNA containing Fapy.dG and its beta-C-nucleoside analogue by formamidopyrimidine DNA glycosylase and MutY. Biochemistry. Aug. 19, 2003;42(32):9755-60.

Xue et al., Facile quantification of lesions derived from 2'-deoxyguanosine in DNA. J Am Chem Soc. Jun. 6, 2007;129(22):7010-1.

Zhu et al., The RAD17 Promoter Sequence Contains a Potential Tail-Dependent G-Quadruplex That Downregulates Gene Expression upon Oxidative Modification. ACS Chem Biol. Sep. 21, 2018;13(9):2577-2584.

* cited by examiner

SEQUENCE LISTING

```
<160> NUMBER OF SEQ ID NOS: 13

<210> SEQ ID NO 1
<211> LENGTH: 15
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (11)..(11)
<223> OTHER INFORMATION: N6-(2-DEOXY-ALPHA,BETA-DERYTHROPENTOFURANOSYL)-
      2,6-DIAMINO-4-HYDROXY-5-FORMAMIDOPYRIMIDINE

<400> SEQUENCE: 1
tttttttttt gtttt                                                         15

<210> SEQ ID NO 2
<211> LENGTH: 30
<212> TYPE: DNA
<213> ORGANISM: Artificial sequence
<220> FEATURE:
<223> OTHER INFORMATION: Synthetic

<400> SEQUENCE: 2
tttaggcgtg gtgatgctgt gtgctatggt                                         30

<210> SEQ ID NO 3
<211> LENGTH: 10
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (10)..(10)
<223> OTHER INFORMATION: N6-(2-DEOXY-ALPHA,BETA-DERYTHROPENTOFURANOSYL)-
      2,6-DIAMINO-4-HYDROXY-5-FORMAMIDOPYRIMIDINE

<400> SEQUENCE: 3
gctgatgcgg                                                               10

<210> SEQ ID NO 4
<211> LENGTH: 12
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (5)..(5)
<223> OTHER INFORMATION: N6-(2-DEOXY-ALPHA,BETA-DERYTHROPENTOFURANOSYL)-
      2,6-DIAMINO-4-HYDROXY-5-FORMAMIDOPYRIMIDINE

<400> SEQUENCE: 4
```
cgcagcgctg cg                                               12

<210> SEQ ID NO 5
<211> LENGTH: 12
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (5)..(5)
<223> OTHER INFORMATION: N6-(2-DEOXY-ALPHA,BETA-DERYTHROPENTOFURANOSYL)-
      2,6-DIAMINO-4-HYDROXY-5-FORMAMIDOPYRIMIDINE

<400> SEQUENCE: 5
gtgcgtgttt gt                                               12

<210> SEQ ID NO 6
<211> LENGTH: 12
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (5)..(5)
<223> OTHER INFORMATION: N6-(2-DEOXY-ALPHA,BETA-DERYTHROPENTOFURANOSYL)-
      2,6-DIAMINO-4-HYDROXY-5-FORMAMIDOPYRIMIDINE

<400> SEQUENCE: 6
aaccggaggc cc                                               12

<210> SEQ ID NO 7
<211> LENGTH: 12
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (8)..(8)
<223> OTHER INFORMATION: N6-(2-DEOXY-ALPHA,BETA-DERYTHROPENTOFURANOSYL)-
      2,6-DIAMINO-4-HYDROXY-5-FORMAMIDOPYRIMIDINE

<400> SEQUENCE: 7
aaccggaggc cc                                               12

<210> SEQ ID NO 8
<211> LENGTH: 16
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (10)..(10)
<223> OTHER INFORMATION: N6-(2-DEOXY-ALPHA,BETA-DERYTHROPENTOFURANOSYL)-
      2,6-DIAMINO-4-HYDROXY-5-FORMAMIDOPYRIMIDINE

<400> SEQUENCE: 8
ggaagcaatg gtacgg                                           16

<210> SEQ ID NO 9
<211> LENGTH: 21
<212> TYPE: DNA
<213> ORGANISM: Artificial sequence
<220> FEATURE:
<223> OTHER INFORMATION: Synthetic
<220> FEATURE:

```
<221> NAME/KEY: modified_base
<222> LOCATION: (11)..(11)
<223> OTHER INFORMATION: N6-(2-DEOXY-ALPHA,BETA-DERYTHROPENTOFURANOSYL)-
      2,6-DIAMINO-4-HYDROXY-5-FORMAMIDOPYRIMIDINE

<400> SEQUENCE: 9
agggcggtgt gggaagaggg a                                              21

<210> SEQ ID NO 10
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (5)..(5)
<223> OTHER INFORMATION: N6-(2-DEOXY-ALPHA,BETA-DERYTHROPENTOFURANOSYL)-
      2,6-DIAMINO-4-HYDROXY-5-FORMAMIDOPYRIMIDINE

<400> SEQUENCE: 10
aaccggaggc ccatcctcac                                                20

<210> SEQ ID NO 11
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (5)..(5)
<223> OTHER INFORMATION: N6-(2-DEOXY-ALPHA,BETA-DERYTHROPENTOFURANOSYL)-
      2,6-DIAMINO-4-HYDROXY-5-FORMAMIDOPYRIMIDINE

<400> SEQUENCE: 11
gtgcgtgttt gtgcctgtcc                                                20

<210> SEQ ID NO 12
<211> LENGTH: 30
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (16)..(16)
<223> OTHER INFORMATION: N6-(2-DEOXY-ALPHA,BETA-DERYTHROPENTOFURANOSYL)-
      2,6-DIAMINO-4-HYDROXY-5-FORMAMIDOPYRIMIDINE

<400> SEQUENCE: 12
tgttcatcat gggtcgtcgg tatatcccat                                     30

<210> SEQ ID NO 13
<211> LENGTH: 16
<212> TYPE: DNA
<213> ORGANISM: Artificial sequence
<220> FEATURE:
<223> OTHER INFORMATION: Synthetic
<220> FEATURE:
<221> NAME/KEY: modified_base
<222> LOCATION: (6)..(6)
<223> OTHER INFORMATION: N6-(2-DEOXY-ALPHA,BETA-DERYTHROPENTOFURANOSYL)-
      2,6-DIAMINO-4-HYDROXY-5-FORMAMIDOPYRIMIDINE

<400> SEQUENCE: 13
ccgacgtcgc atcagc                                                    16
```

SOLID-PHASE SYNTHESIS OF OLIGONUCLEOTIDES CONTAINING N6-(2-DEOXY-ALPHA,BETA-DERYTHROPENTOFURANOSYL)-2,6-DIAMINO-4-HYDROXY-5-FORMAMIDOPYRIMIDINE (FAPY·DG)

CROSS-REFERENCE TO RELATED APPLICATIONS

The present application claims the priority benefit of U.S. Patent Application Ser. No. 62/966,655, filed Jan. 28, 2020, which is incorporated by reference in its entirety.

FEDERALLY SPONSORED RESEARCH OR DEVELOPMENT

This invention was made with government support under ES027558 awarded by the National Institutes of Health. The government has certain rights in the invention.

BACKGROUND

N6-(2-Deoxy-α,β-D-erythropentofuranosyl)-2,6-diamino-4-hydroxy-5-formamidopyrimidine (Fapy·dG) is produced from 2'-deoxyguanosine under oxidizing conditions from a common intermediate that leads to 7,8-dihydro-8-oxo-2'-deoxyguanosine (8-OxodGuo). The impact of Fapy·dG on DNA structure and function is much less well understood than that of 8-OxodGuo. This lack of understanding is largely due to the significantly greater difficulty in synthesizing oligonucleotides containing Fapy·dG than 8-OxodGuo. A synthetic approach for preparing oligonucleotides containing Fapy·dG would facilitate intensive studies of this important lesion in DNA.

SUMMARY

In some aspects, the presently disclosed subject matter provides a method for synthesizing an oligonucleotide, the method comprising: (a) providing a nucleoside phosphoramidite comprising a 2'-deoxyribose moiety having a 3'-hydroxyl position and a 5'-hydroxyl position, wherein the nucleoside phosphoramidite has a dimethoxytrityl protecting group at the 3'-hydroxyl position and a phosphoramidite moiety at the 5'-hydroxyl position; and (b) contacting the nucleoside phosphoramidite of (a) with one or more nucleoside residues attached to a solid phase support to form a solid support-bound product.

In particular aspects, the nucleoside phosphoramidite of (a) has the following structure:

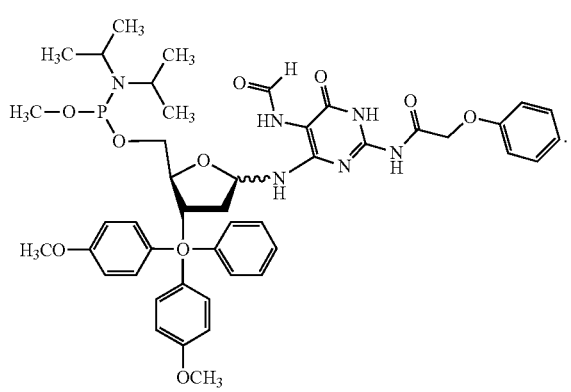

(1)

In some aspects, the solid phase support comprises a universal support. In other aspects, the solid phase support comprises one or more nucleoside or nucleoside analogues. In certain aspects, the one or more nucleoside residues attached to the solid phase support comprise one or more thymidines and a single Fapy·dG moiety on a reverse 3'-thymidine support comprising a succinate linkage between the 5'-hydroxyl group and a long chain alkylamine linker to the solid phase support:

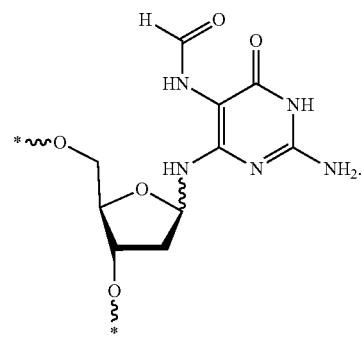 [SMILES: *OC[C@H]1O[C@@H](Nc2nc(N)[nH]c(=O)c2NC=O)C[C@H]1O*]

In some aspects, the method further comprises detritylating the nucleoside phosphoramidite having a dimethoxytrityl protecting group at the 3'-hydroxyl position. In such aspects, the method comprises contacting the nucleoside phosphoramidite having a dimethoxytrityl protecting group at the 3'-hydroxyl position with trichloroacetic acid (TCA) or dichloroacetic acid (DCA). In further aspects, the method comprises removing a dimethoxytrityl cation formed during the detritylating of the nucleoside phosphoramidite having a dimethoxytrityl protecting group at the 3'-hydroxyl position.

In some aspects, the method further comprises contacting the nucleoside phosphoramidite of (a) with an activator before contacting it with the one or more nucleoside residues attached to a solid phase support. In certain aspects, the activator is selected from the group consisting of 4,5-dicyanoimidazole, 1H-tetrazole, 5-ethylthio-1H-tetrazole, 2-benzylthiotetrazole, 5-(p-nitrophenyl)-1H-tetrazole, and benzimidazolium triflate. In particular aspects, the activator is 4,5-dicyanoimidazole.

In some aspects, the method further comprises contacting the solid support-bound product with an oxidizing agent to form an oxidized solid support-bound product. In certain aspects, the oxidizing agent is selected from the group consisting of tert-butyl hydroperoxide (t-BuOOH), $I_2$/water, and (1S)-(+)-(10-camphorsulfonyl)-oxaziridine (CSO). In particular aspects, the oxidizing agent is tert-butyl hydroperoxide (t-BuOOH). In some aspects, the oxidized product comprises a phosphate triester. In some aspects, the method further comprises capping the solid support-bound product of (b). In certain aspects, the method comprises contacting treating the solid support-bound product with a solution comprising pivalic anhydride/lutidine/tetrahydrofuran (THF).

In further aspects, the method comprises demethylating the phosphate triester. In certain aspects, the demethylating of the phosphate triester comprises contacting the phosphate triester with disodium 2-carbamoyl-2-cyanoethylene-1,1-dithiolate trihydrate.

In some aspects, the method further comprises deprotecting and/or cleaving the solid support-bound product of (b). In certain aspects, the method comprises contacting the solid support-bound product of (b) with one or more of aqueous ammonia, NaOH, $K_2CO_3$, t-butylamine, and combinations thereof.

In some aspects, the method further comprises purifying the deprotected and/or cleaved solid support-bound product of (b). In certain aspects, the method comprises purifying the deprotected and/or cleaved solid support-bound product of (b) with gel electrophoresis or reversed-phase high-performance liquid chromatography (HPLC).

In particular aspects, the one or more nucleoside residues attached to the solid phase support comprise at least one N6-(2-Deoxy-α,β-D-erythropentofuranosyl)-2,6-diamino-4-hydroxy-5-formamidopyrimidine (Fapy·dG) moiety:

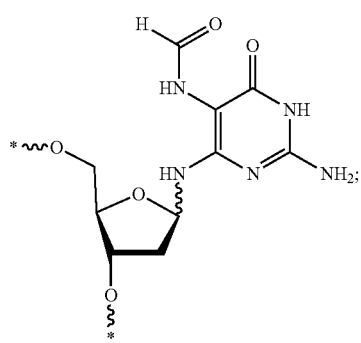 [SMILES: *OC[C@H]1O[C@@H](Nc2nc(N)[nH]c(=O)c2NC=O)C[C@H]1O*]

wherein * denotes a point of attachment of the Fapy·dG moiety to one or more other nucleosides.

In other aspects, the one or more nucleoside residues attached to the solid phase support comprise at least one N4-(2-Deoxy-α,β-D-erythropentofuranosyl)-4,6-diamino-5-formamidopyrimidine (Fapy·dA) moiety:

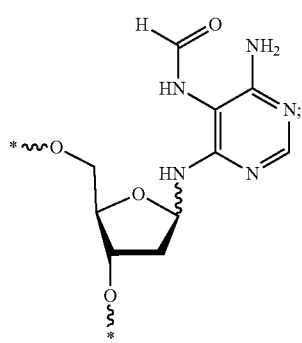 [SMILES: *OC[C@H]1O[C@@H](Nc2ncnc(N)c2NC=O)C[C@H]1O*]

wherein * denotes a point of attachment of the Fapy·dA moiety to one or more other nucleosides.

In certain aspects, the synthesized oligonucleotide comprises at least one Fapy·dG moiety. In other aspects, the synthesized oligonucleotide comprises at least one Fapy·dA moiety.

In particular aspects, the synthesized oligonucleotide comprises one or more nucleoside selected from the group consisting of adenosine (A), guanosine (G), cytidine (C), and thymidine (T). In yet more particular aspects, the synthesized oligonucleotide is selected from the group consisting of:

5'-d($T_{10}$x$T_4$) SEQ ID NO: 1    17

5'-d(TTT AGG CGT GGT GAT GCT GTG TGC TAT GGT) SEQ ID NO: 2    18

5'-d(GCT GAT GCG X) SEQ ID NO: 3    19

5'-d(CGC AXC GCT GCG) SEQ ID NO: 4    20

5'-d(GTG CXT GTT TGT) SEQ ID NO: 5    21

5'-d(AAC CXG AGG CCC) SEQ ID NO: 6    22

5'-d(AAC CGG AXG CCC) SEQ ID NO: 7    23

5'-d(GGA AGC AAT XGT ACG G) SEQ ID NO: 8    24

5'-d(CCG ACX TCG CAT CAG C) SEQ ID NO: 13    25

5'-d(AGG GCG GTG TXG GAA GAG GGA) SEQ ID NO: 9    26

5'-d(AAC CXG AGG CCC ATC CTC AC) SEQ ID NO: 10    27

5'-d(GTG CXT GTT TGT GCC TGT CC) SEQ ID NO: 11    28

5'-d(TGT TCA TCA TGG GTC XTC GGT ATA TCC CAT) SEQ ID NO: 12    29 x=Fapy·dG.

In other aspects, the presently disclosed subject matter provides a method for synthesizing an oligonucleotide, the method comprising: (a) providing a nucleoside phosphoramidite comprising a 2'-deoxyribose moiety having a 3'-hydroxyl position and a 5'-hydroxyl position, wherein the nucleoside phosphoramidite has a dimethoxytrityl protecting group at the 3'-hydroxyl position and a phosphoramidite moiety at the 5'-hydroxyl position; (b) detritylating the nucleoside phosphoramidite having a dimethoxytrityl protecting group at the 3'-hydroxyl position of (a) to form a detritylated nucleoside phosphoramidite; (c) contacting the detritylated nucleoside phosphoramidite of (b) with an activator to form an activated detritylated nucleoside phosphoramidite; (d) contacting the activated detritylated nucleoside phosphoramidite of (c) with one or more nucleoside residues attached to a solid phase support to form a solid support-bound product; (e) contacting the solid support-bound product of (d) with an oxidizing agent to form an oxidized solid support-bound product; (f) capping the oxidized solid support-bound product of (e) to form a capped solid support-bound product; and (g) deprotecting and/or cleaving the capped solid support-bound product of (f).

In yet other aspects, the presently disclosed method provides a method for preparing N6-(2-Deoxy-α,β-D-erythropentofuranosyl)-2,6-diamino-4-hydroxy-5-formamidopyrimidine (Fapy·dG) phosphoramidite (1):

(1)

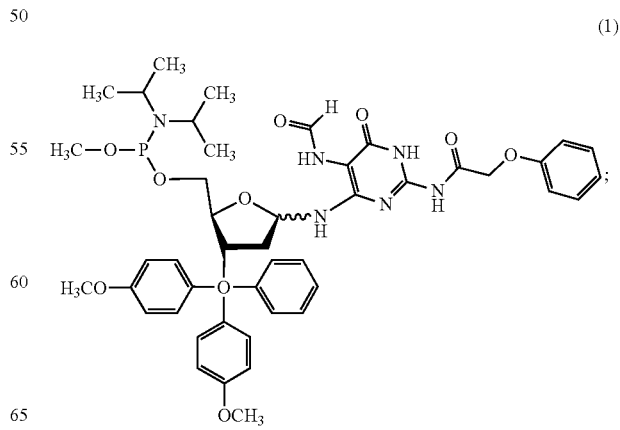

the method comprising:

(a) providing a compound 9:

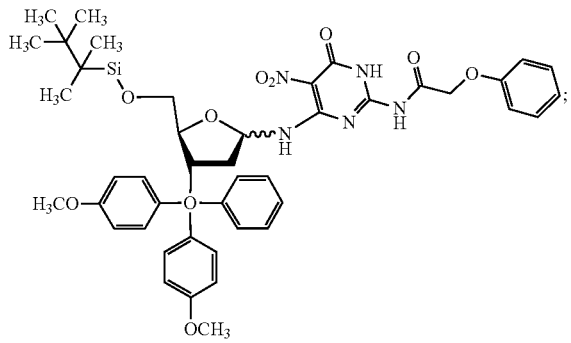
(9)

(b) contacting compound (9) with diphenylcarbamoyl chloride, followed by triethylamine (Et₃N) to yield compound (14):

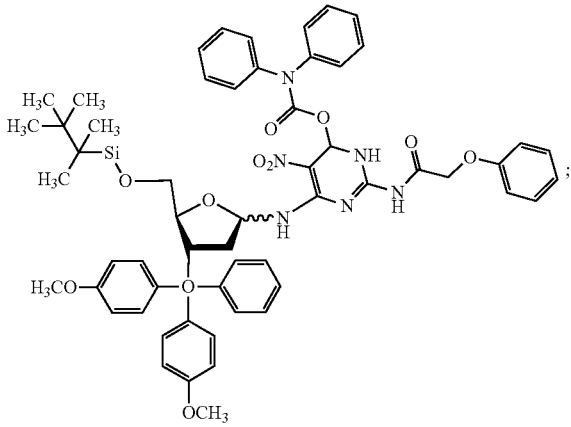
(14)

(c) contacting compound (14) with Et₃N·3HF to yield compound (15):

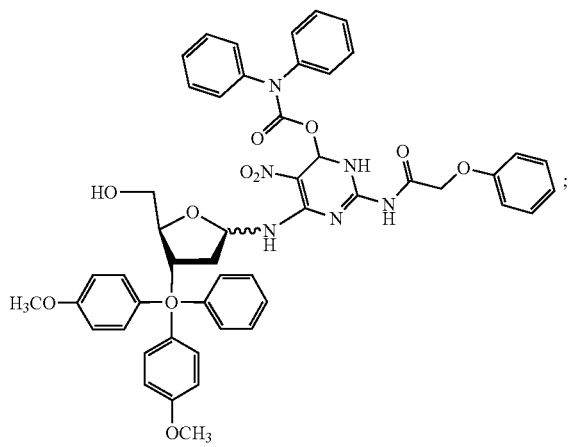
(15)

(d) contacting compound (15) with N, N-diisopropylethylamine (DIPEA), followed by diisopropylmethylphosphanamidic chloride to yield compound (16):

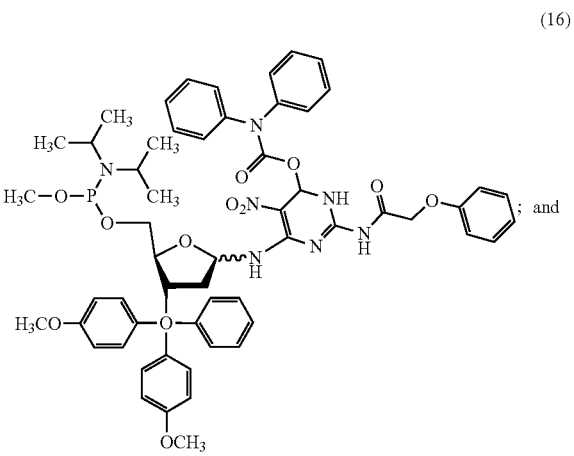
(16)

; and (e) contacting compound (16) with:
 (i) DIPEA and palladium on carbon; and
 (ii) pressurizing with H₂; and
 (iii) followed by contacting with pivalic formic anhydride to form (1).

In even yet other aspects, the presently disclosed subject matter provides a compound comprising the following structure:

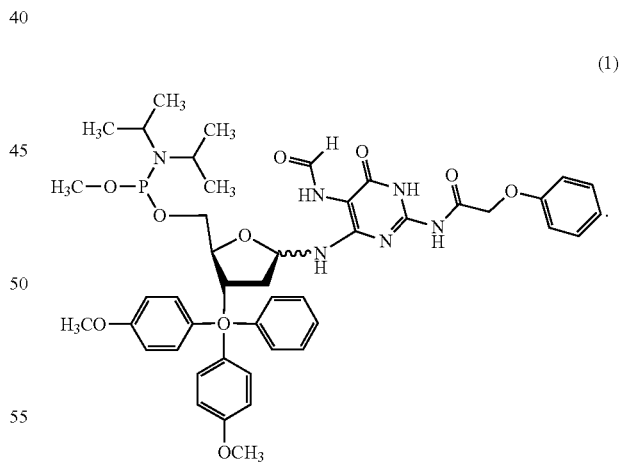
(1)

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1:
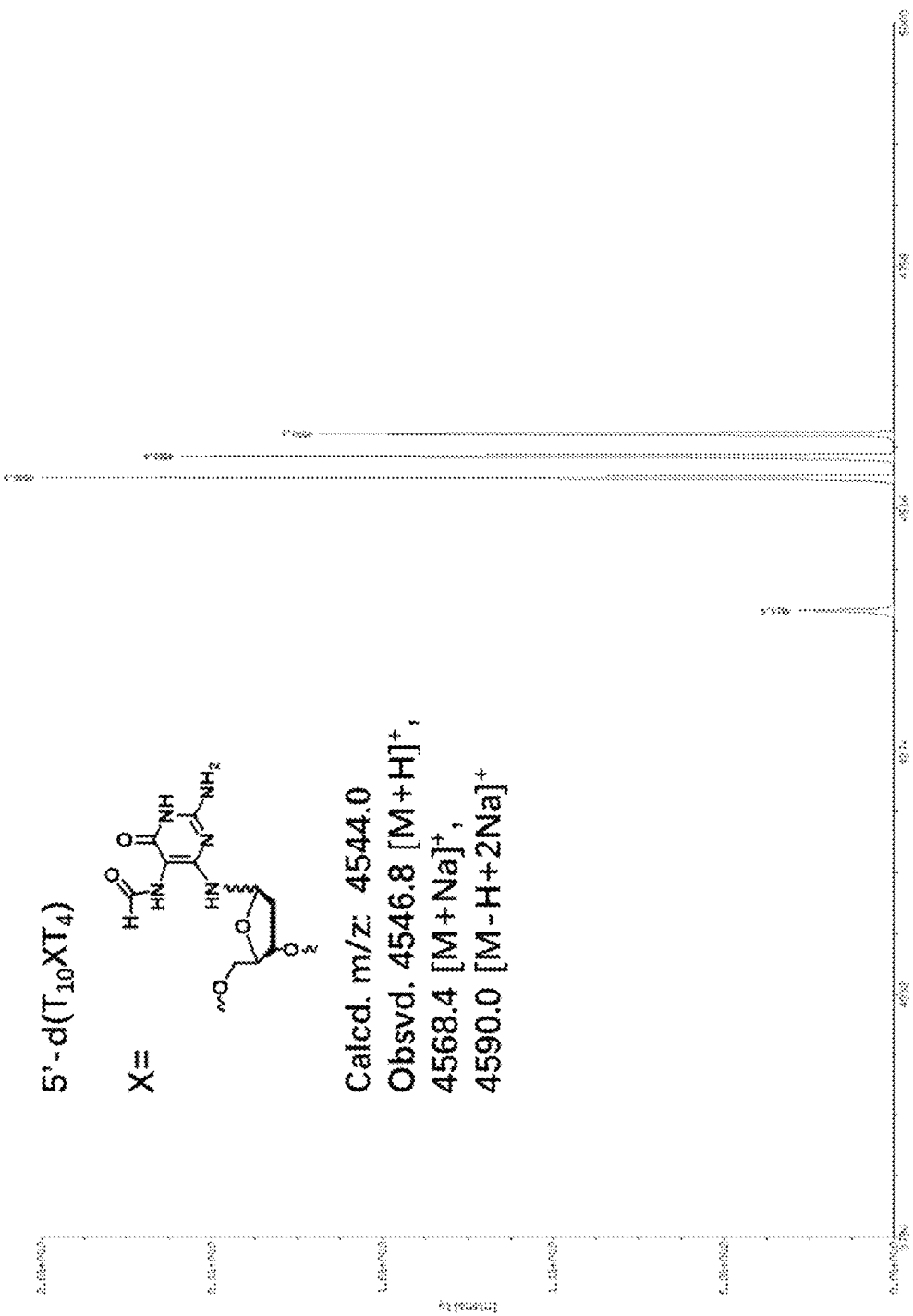
Figure 2:
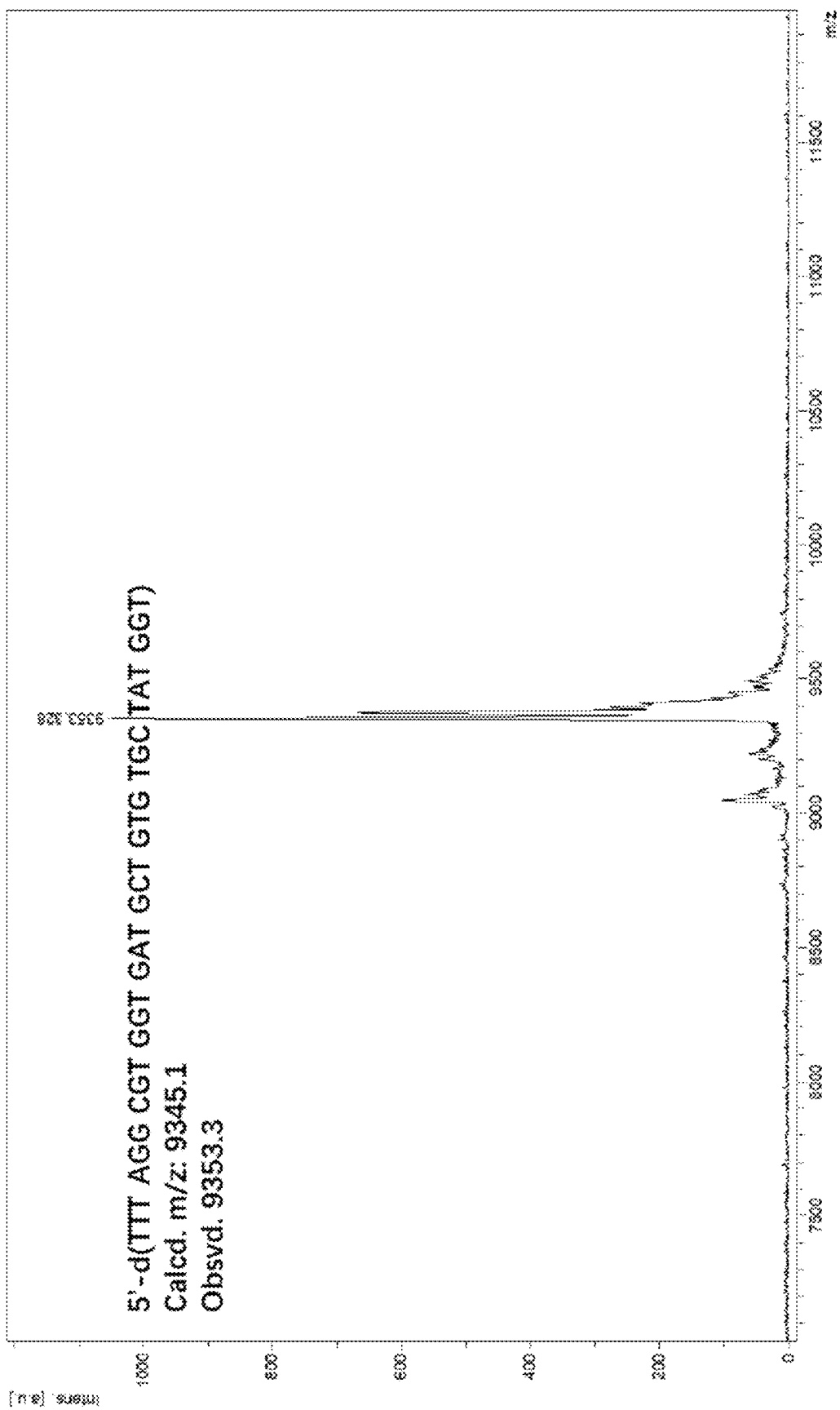
Figure 3:
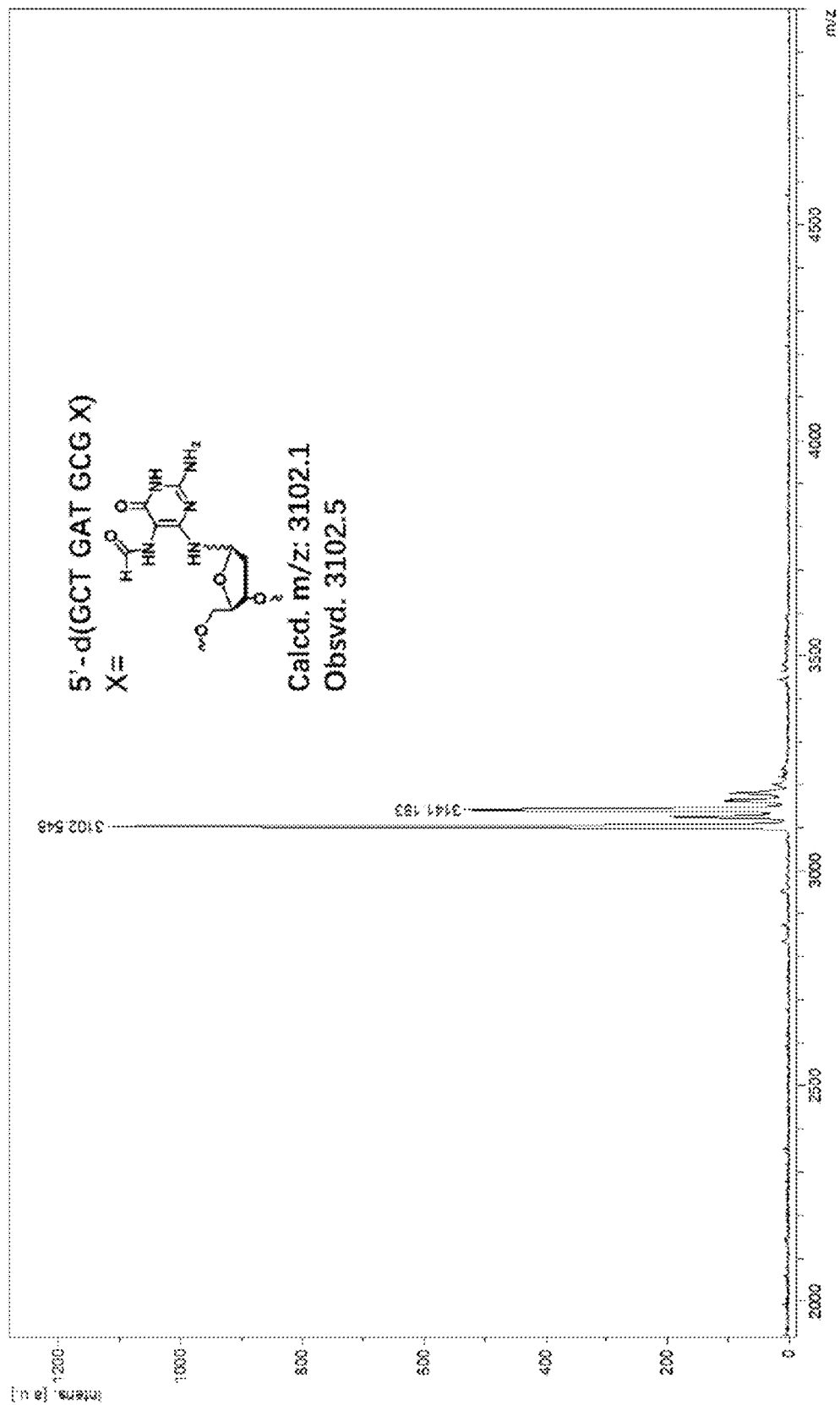
Figure 4:
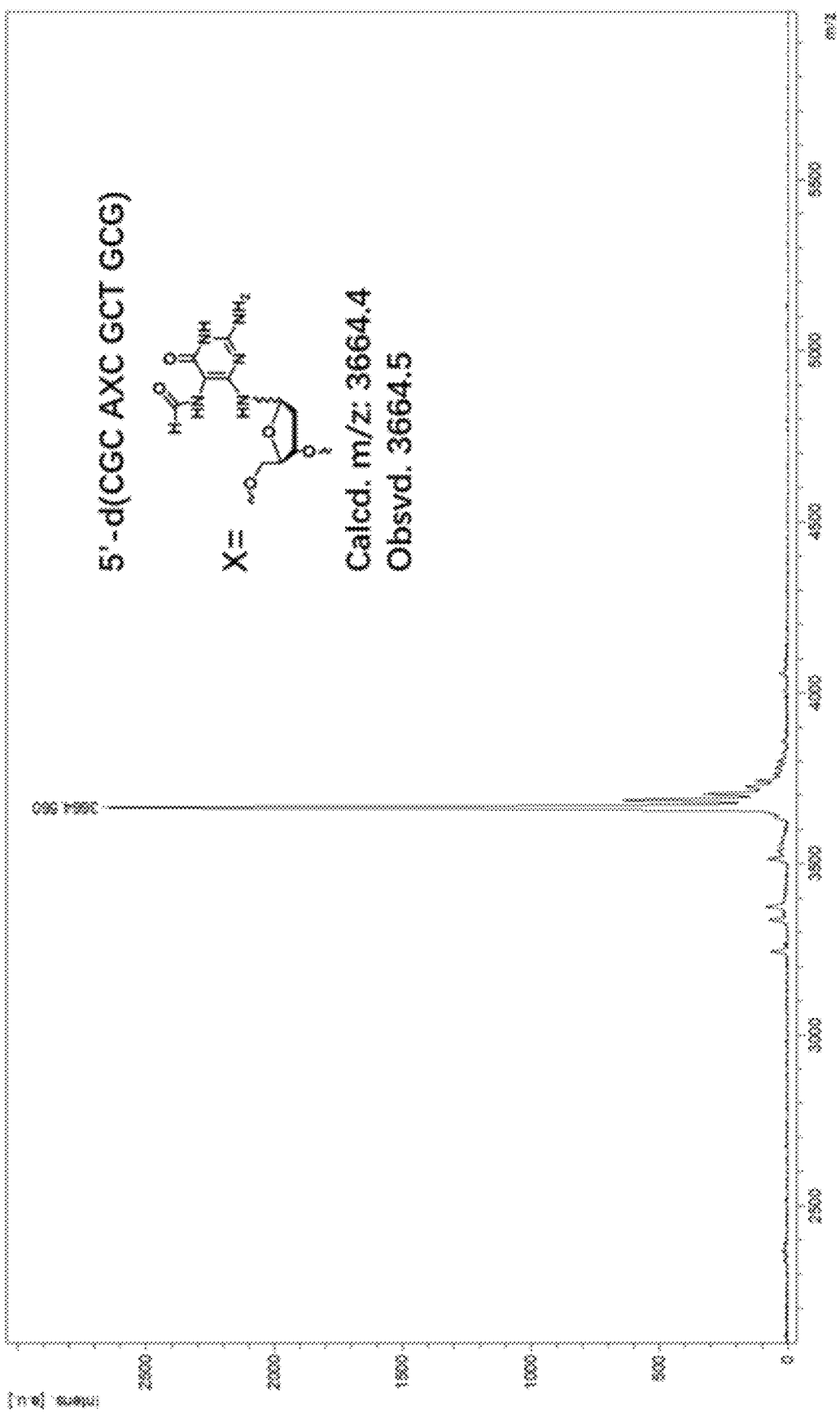
Figure 5:
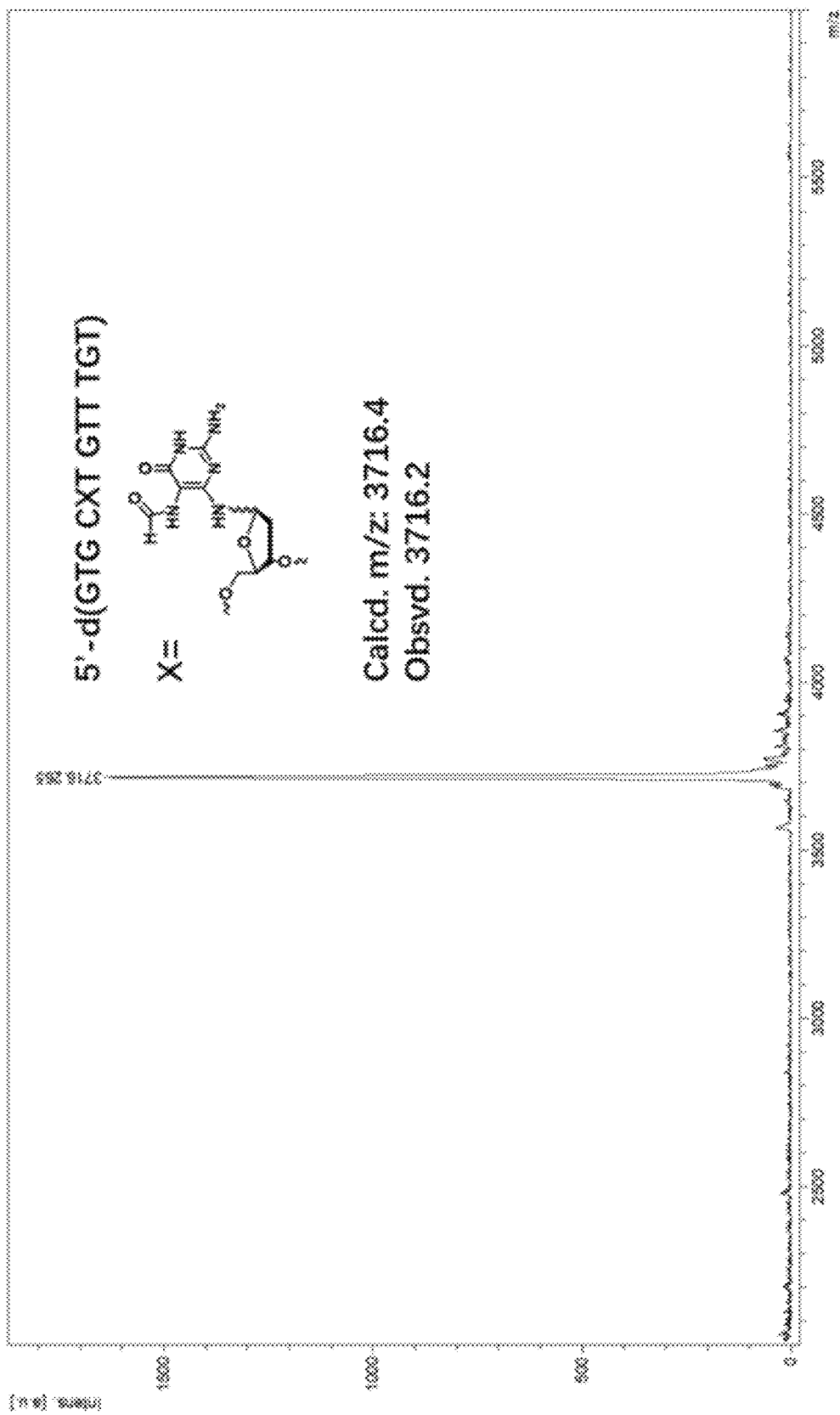
Figure 6:
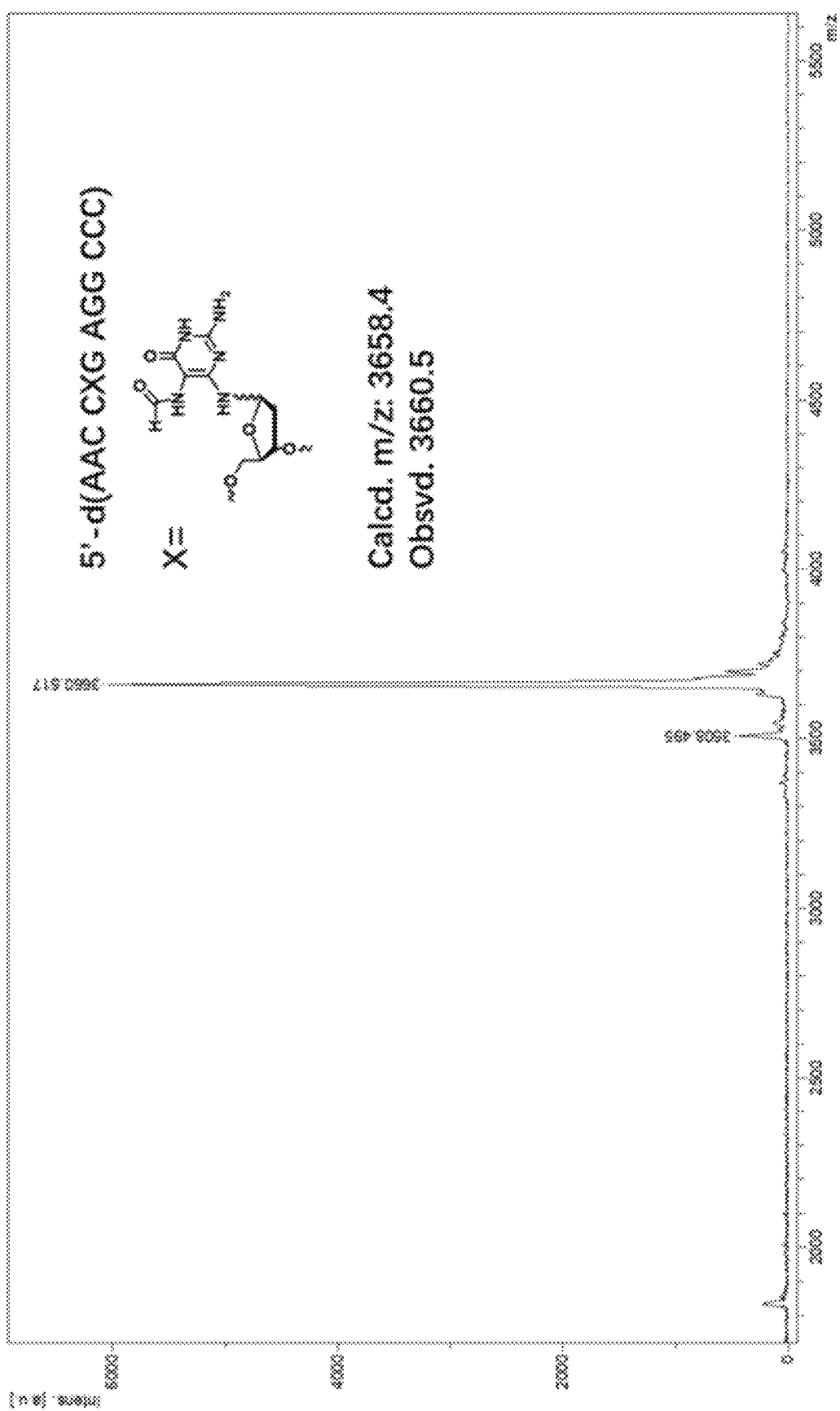
Figure 7:
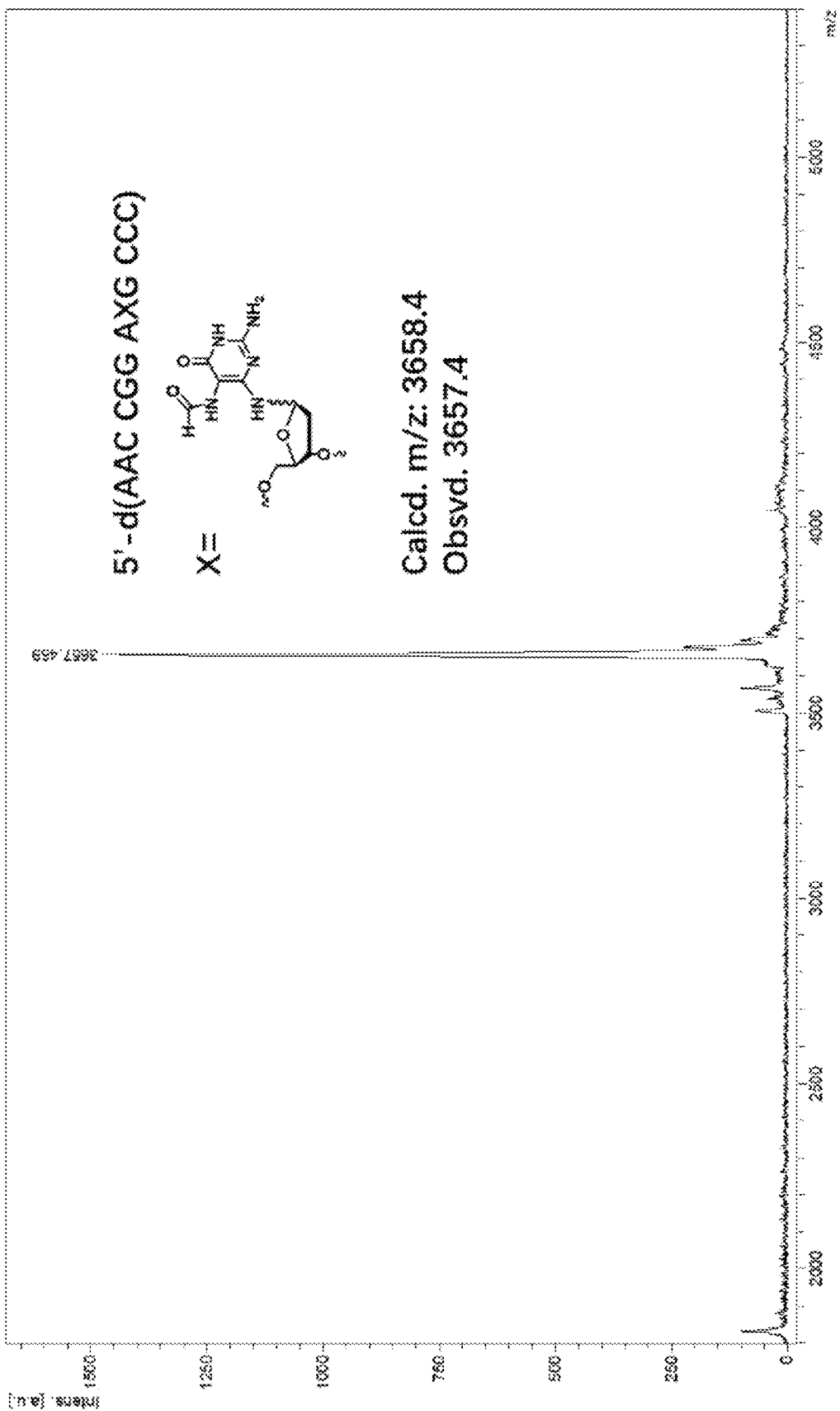
Figure 8:
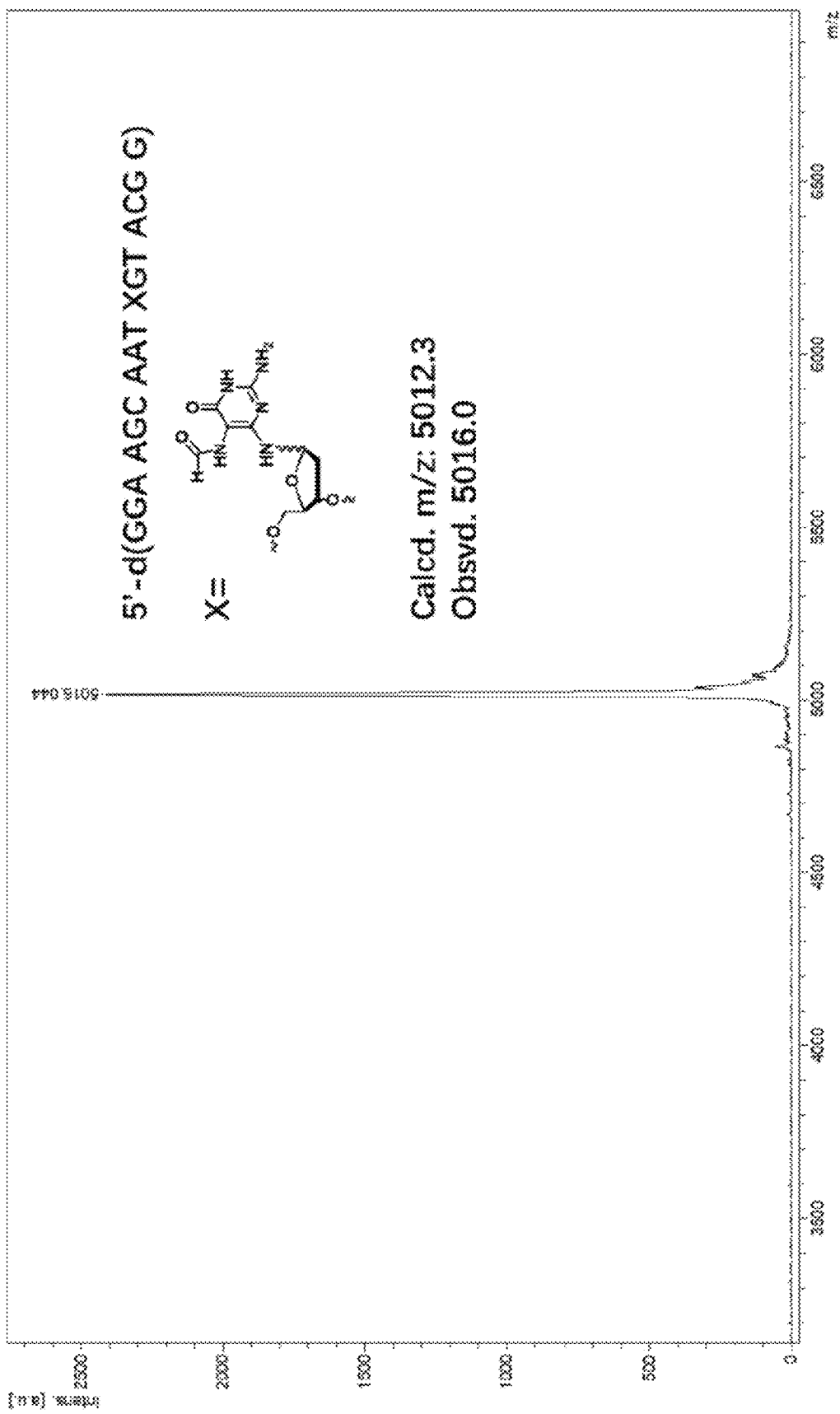
Figure 9:
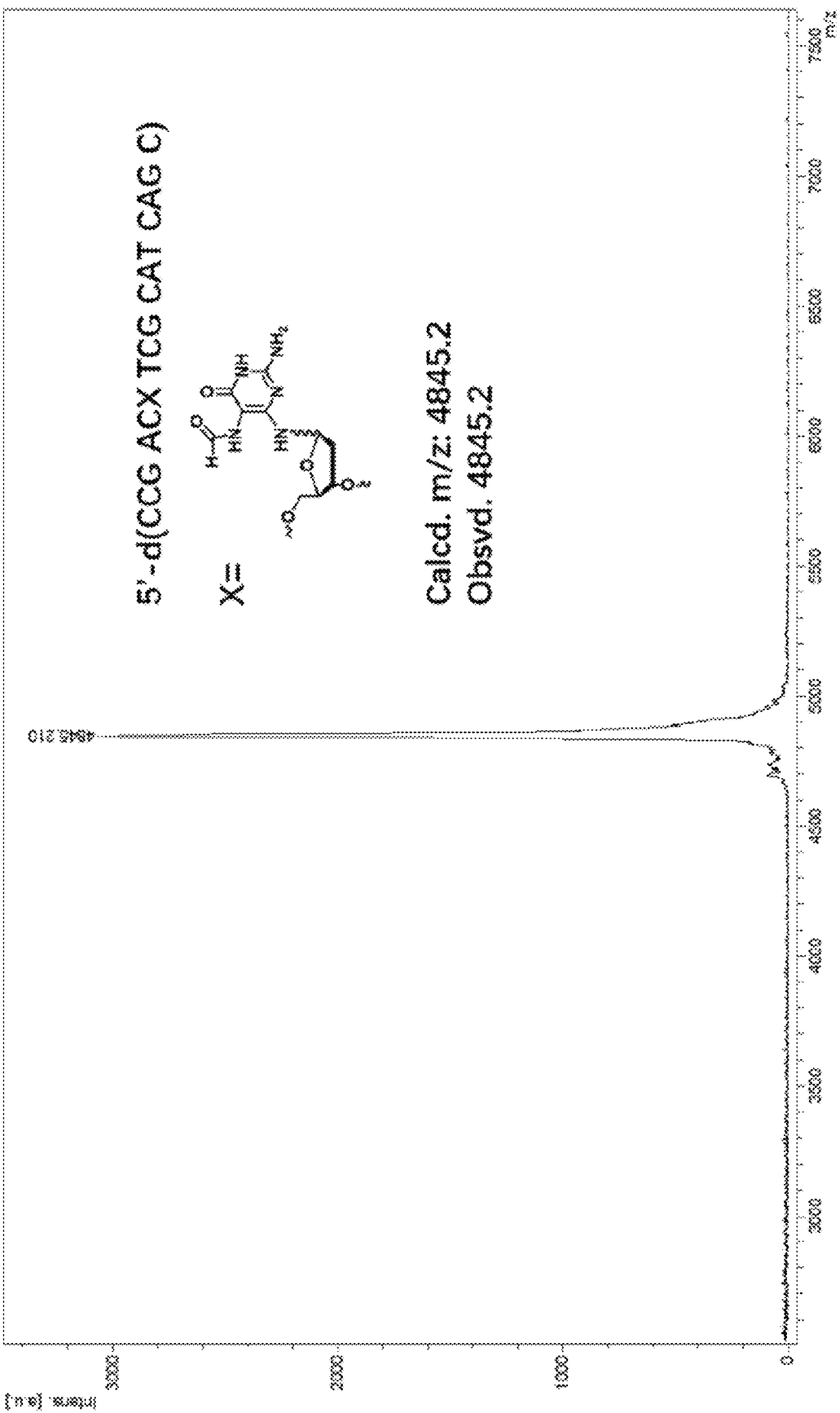
Figure 10:
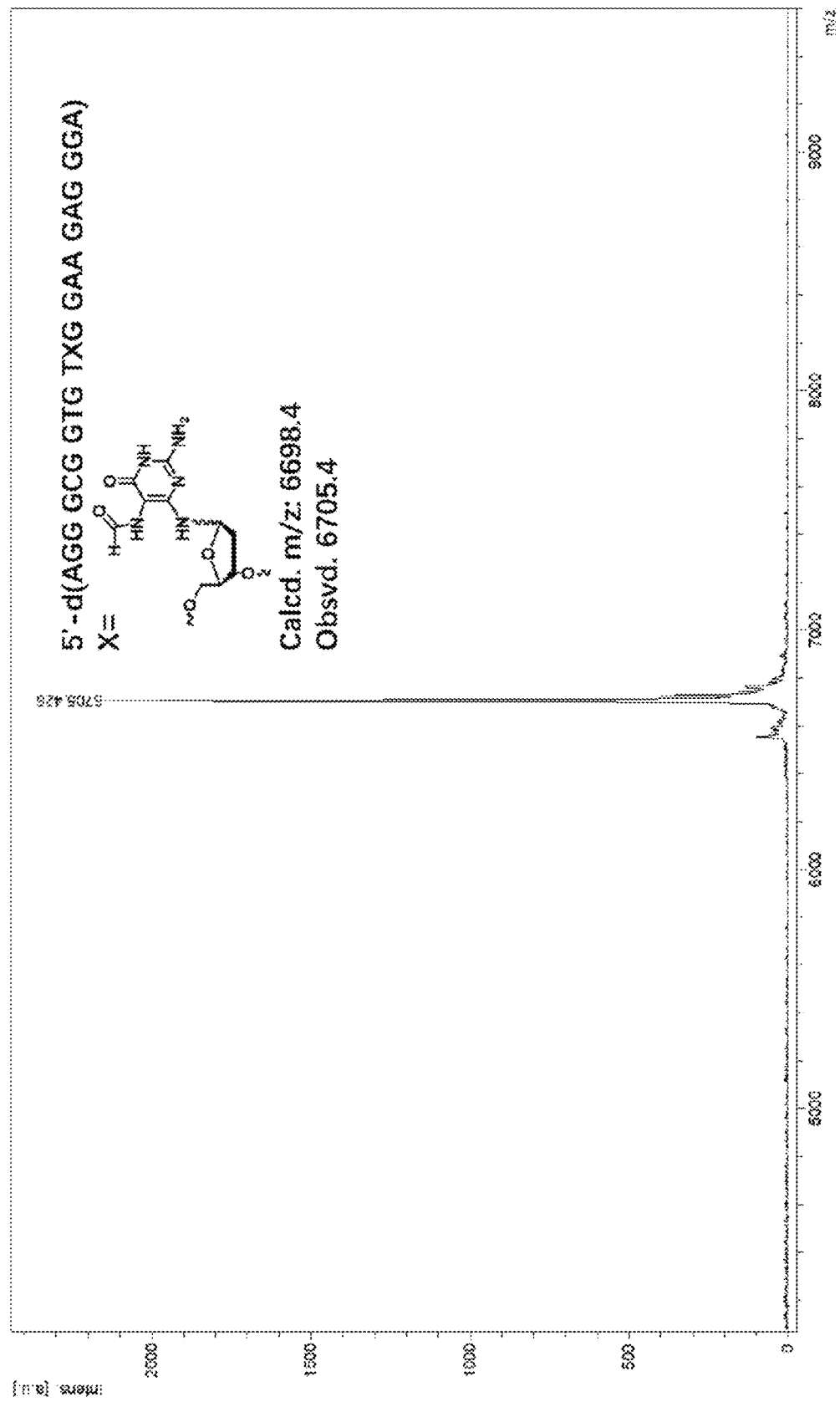
Figure 11:
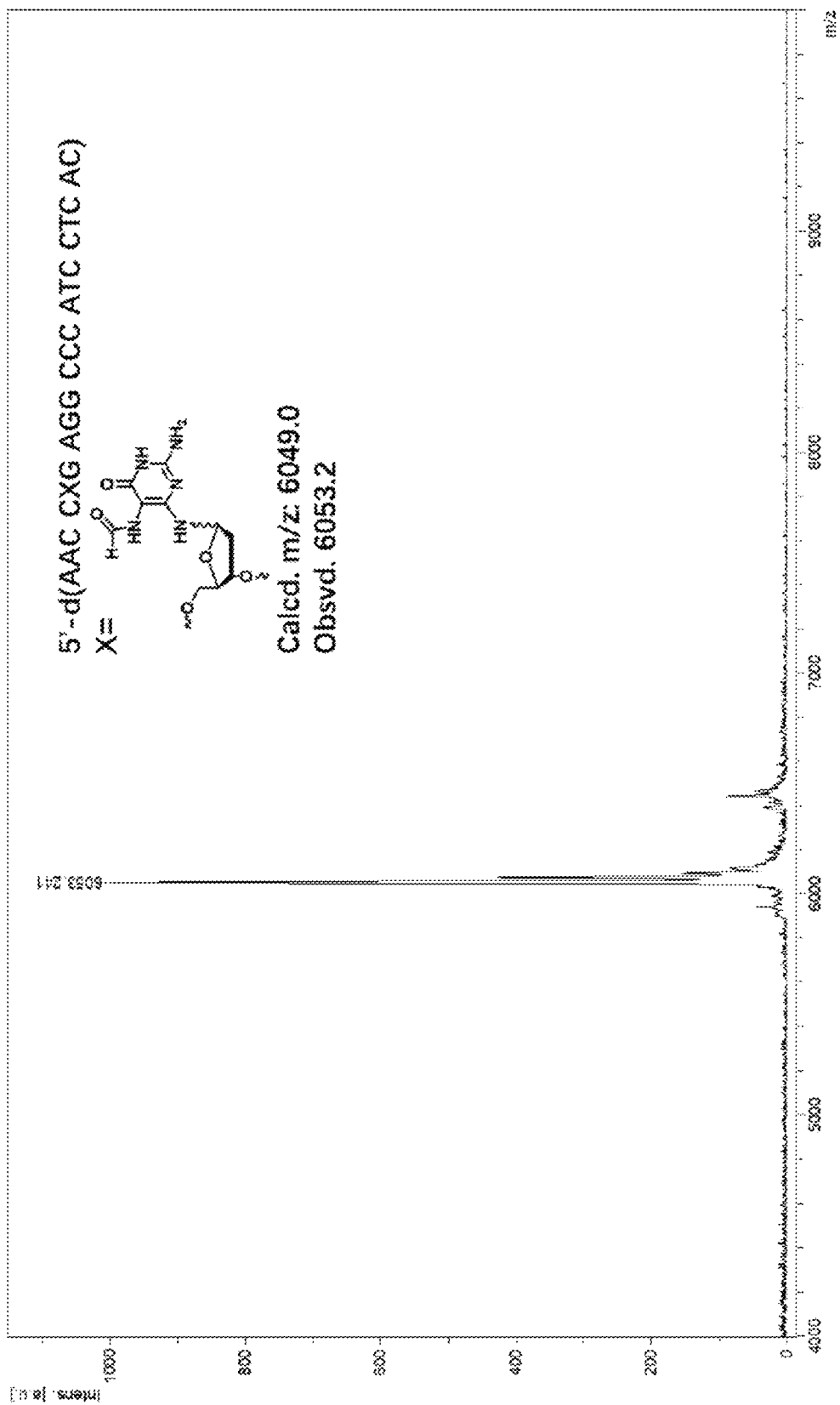
Figure 12:
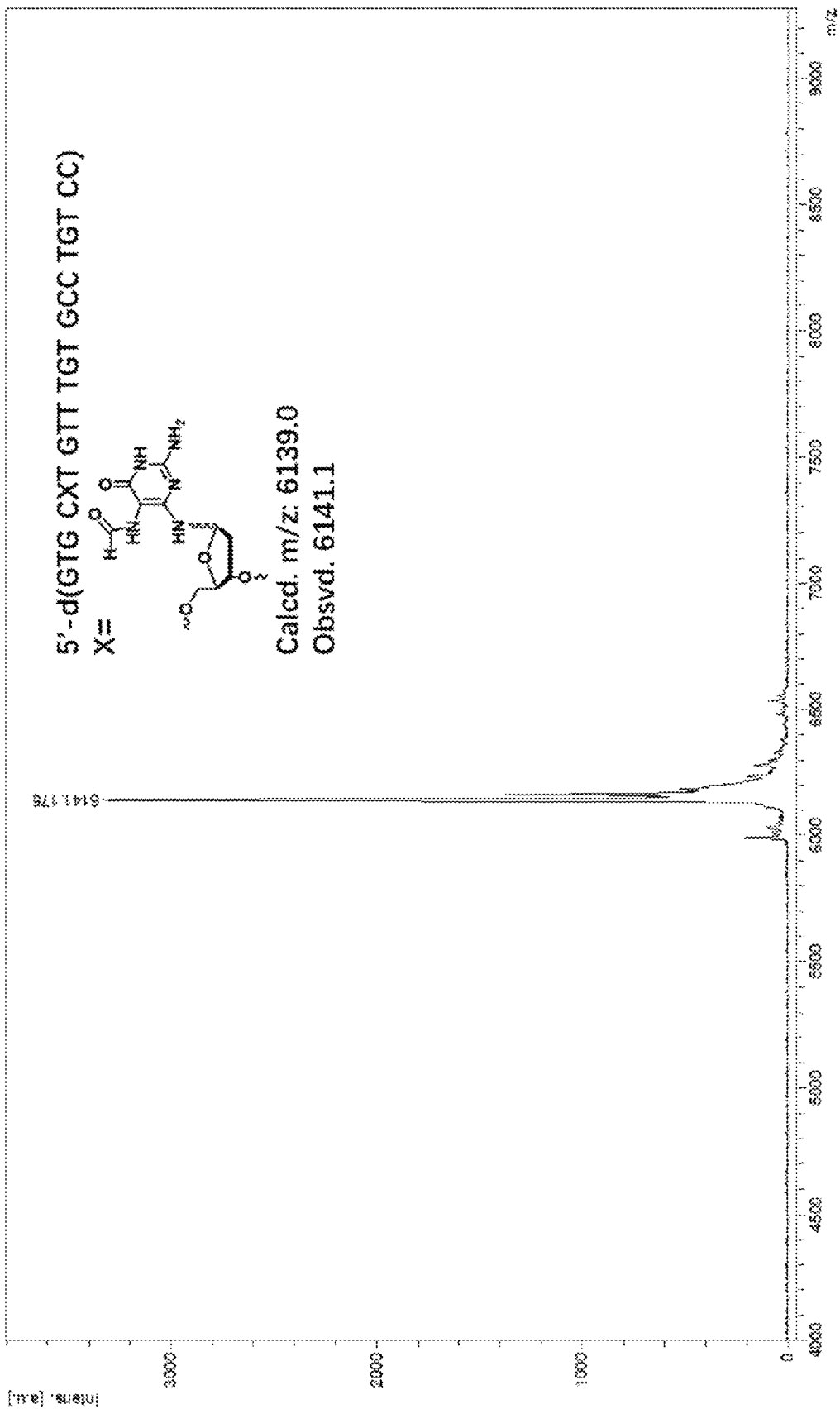
Figure 13:
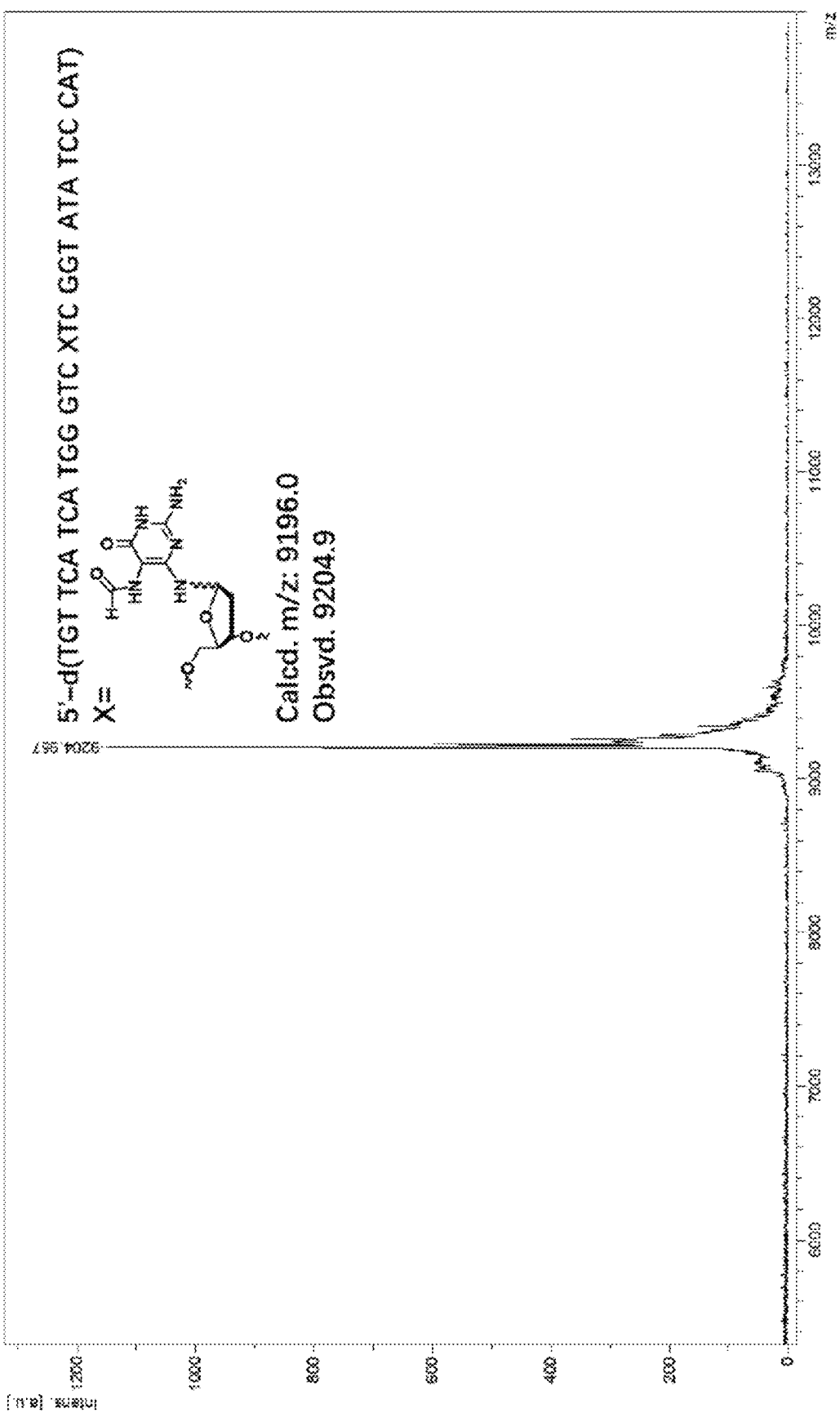
Figure 14:
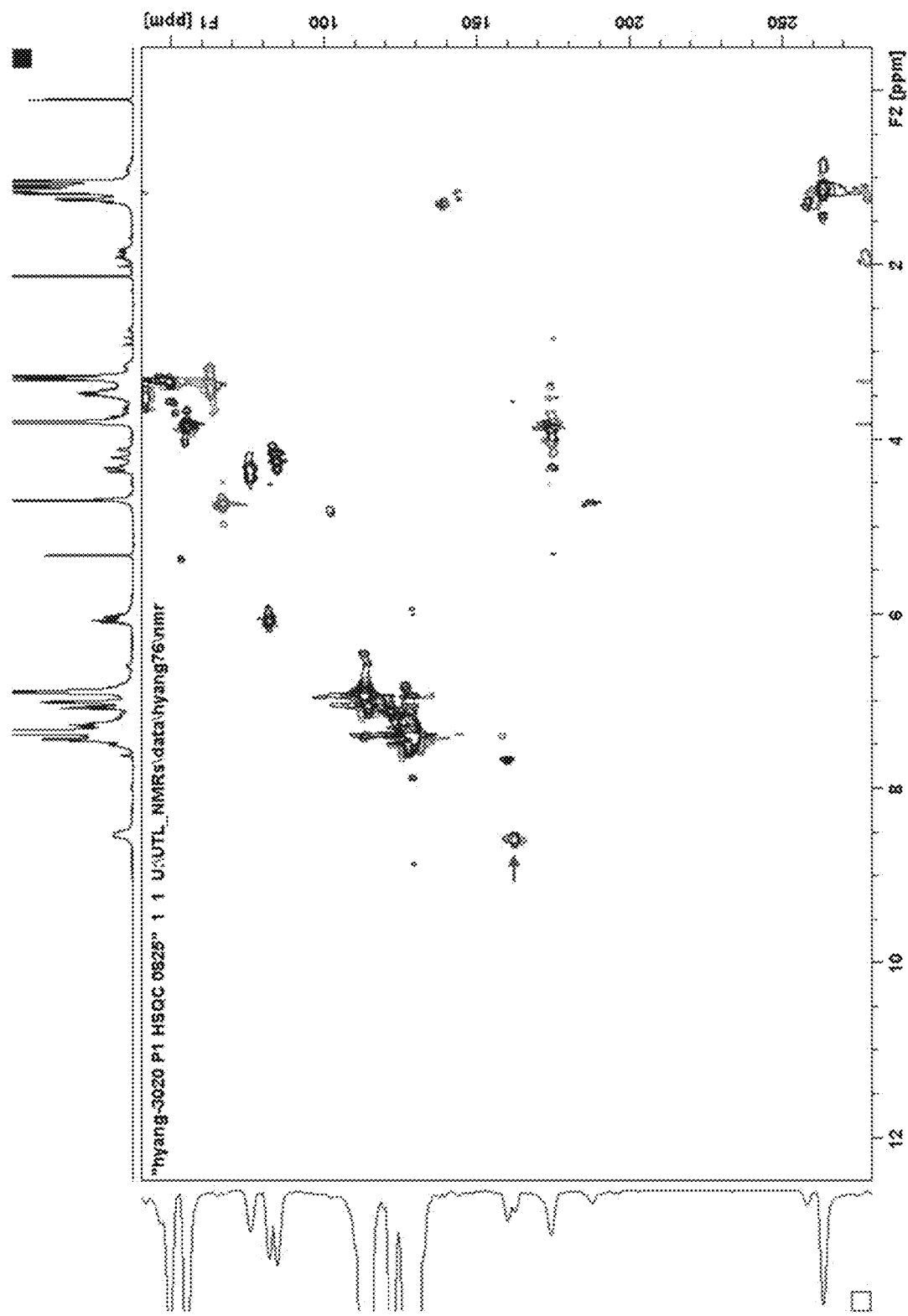

Having thus described the presently disclosed subject matter in general terms, reference will now be made to the accompanying Figures, which are not necessarily drawn to scale, and wherein:

FIG. 1 is an ESI-MS of 17;

FIG. 2 is an MALDI-TOF MS of 18;

FIG. 3 is an MALDI-TOF MS of 19;

FIG. 4 is an MALDI-TOF MS of 20;

FIG. 5 is an MALDI-TOF MS of 21;

FIG. 6 is an MALDI-TOF MS of 22;

FIG. 7 is an MALDI-TOF MS of 23;

FIG. 8 is an MALDI-TOF MS of 24;

FIG. 9 is an MALDI-TOF MS of 25;

FIG. 10 is an MALDI-TOF MS of 26;

FIG. 11 is an MALDI-TOF MS of 27;

FIG. 12 is an MALDI-TOF MS of 28;

FIG. 13 is an MALDI-TOF MS of 29;

FIG. 14 is a $^1$H-$^{13}$C HSQC NMR spectrum of 1 (less polar); and

Figure 15:
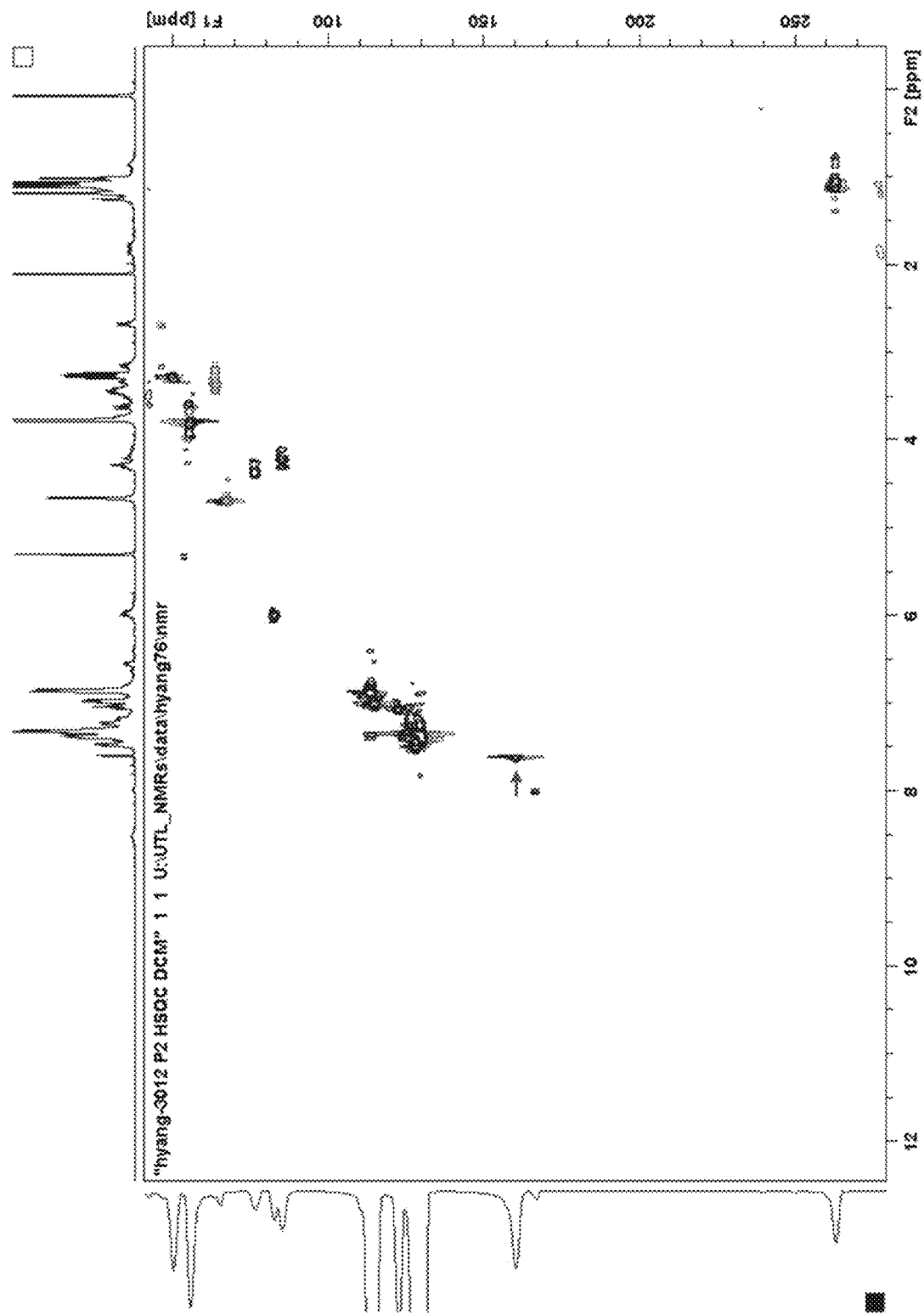

FIG. 15 is $^1$H-$^{13}$C HSQC NMR spectrum of 1 (more polar).

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Solid-Phase Synthesis of Oligonucleotides Containing N6-(2-Deoxy-Alpha,Beta-Derythropentofuranosyl)-2,6-Diamino-4-Hydroxy-5-Formamidopyrimidine (Fapy·dG)

In some embodiments, the presently disclosed subject matter provides a method for synthesizing an oligonucleotide, the method comprising: (a) providing a nucleoside phosphoramidite comprising a 2'-deoxyribose moiety having a 3'-hydroxyl position and a 5'-hydroxyl position, wherein the nucleoside phosphoramidite has a dimethoxytrityl protecting group at the 3'-hydroxyl position and a phosphoramidite moiety at the 5'-hydroxyl position; and (b) contacting the nucleoside phosphoramidite of (a) with one or more nucleoside residues attached to a solid phase support to form a solid support-bound product.

In representative embodiments, the nucleoside phosphoramidite of (a) has the following structure:

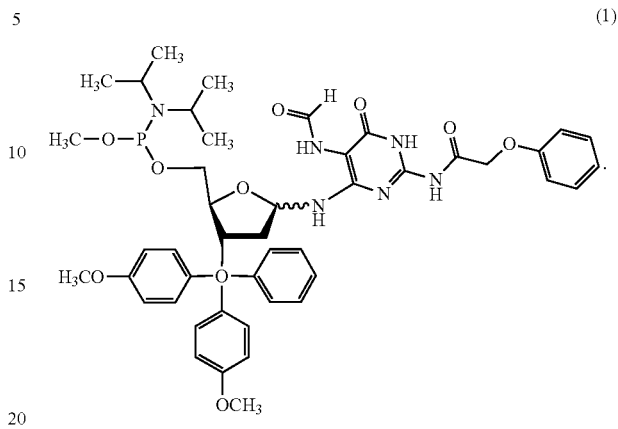

(1)

In some embodiments, the solid phase support comprises a universal support. In other embodiments, the solid phase support comprises one or more nucleoside or nucleoside analogues. In certain embodiments, the one or more nucleoside residues attached to the solid phase support comprise one or more thymidines and a single Fapy·dG moiety on a reverse 3'-thymidine support comprising a succinate linkage between the 5'-hydroxyl group and a long chain alkylamine linker to the solid phase support:

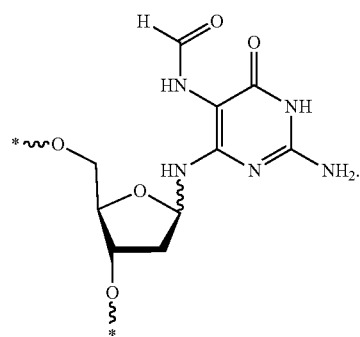 [SMILES: *OC[C@H]1O[C@@H](Nc2nc(N)[nH]c(=O)c2NC=O)C[C@H]1O*]

Solid phase supports known in the art are suitable for use with the presently disclosed methods. In particular embodiments, the solid phase support comprises UnyLinker™ (Chemgenes). Briefly, the UnyLinker™ solid phase support includes the following moiety:

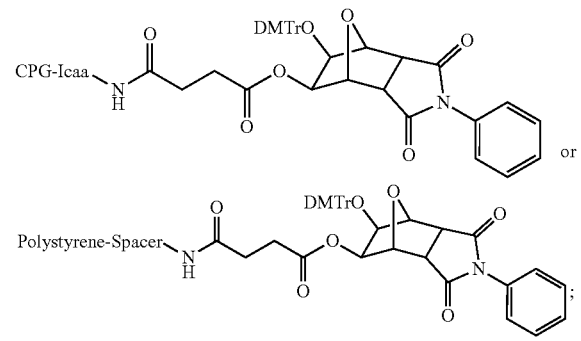

which can be bound to solid supports known in the art, including, but not limited to long chain alkylamine-controlled pore glass (LCAA-CPG), polystyrene, NittoPhase, and OligoPrep solid supports. See, e.g., Ravikumar et al., 2008.

In some embodiments, the method further comprises detritylating the nucleoside phosphoramidite having a dimethoxytrityl protecting group at the 3'-hydroxyl position. Such methods comprise contacting the nucleoside phosphoramidite having a dimethoxytrityl protecting group at the 3'-hydroxyl position with trichloroacetic acid (TCA) or dichloroacetic acid (DCA). In some embodiments, the method further comprises removing, for example by washing, a dimethoxytrityl cation formed during the detritylating of the nucleoside phosphoramidite having a dimethoxytrityl protecting group at the 3'-hydroxyl position.

In some embodiments, the method further comprises contacting the nucleoside phosphoramidite of (a) with an activator before contacting it with the one or more nucleoside residues attached to a solid phase support. In certain embodiments, the activator is selected from the group consisting of 4,5-dicyanoimidazole, 1H-tetrazole, 5-ethylthio-1H-tetrazole, 2-benzylthiotetrazole, 5-(p-nitrophenyl)-1H-tetrazole, and benzimidazolium triflate. In particular embodiments, the activator is 4,5-dicyanoimidazole. Other suitable activators are provided in Wei, Xia (2013). "Coupling activators for the oligonucleotide synthesis via phosphoramidite approach". Tetrahedron. 69 (18): 3615-3637.

In some embodiments, the method further comprises contacting the solid support-bound product with an oxidizing agent to form an oxidized solid support-bound product. In certain embodiments, the oxidizing agent is selected from the group consisting of tert-butyl hydroperoxide (t-BuOOH), I2/water, and (1S)-(+)-(10-camphorsulfonyl)-oxaziridine (CSO). In particular embodiments, the oxidizing agent is tert-butyl hydroperoxide (t-BuOOH). In certain embodiments, the oxidized product comprises a phosphate triester.

In some embodiments, the method further comprises capping the solid support-bound product of (b). In certain embodiments, the method comprises contacting treating the solid support-bound product with a solution comprising pivalic anhydride/lutidine/tetrahydrofuran (THF).

In further embodiments, the presently disclosed method comprises demethylating the phosphate triester. In particular embodiments, the demethylating of the phosphate triester comprises contacting the phosphate triester with disodium 2-carbamoyl-2-cyanoethylene-1,1-dithiolate trihydrate.

In some embodiments, the method further comprises deprotecting and/or cleaving the solid support-bound product of (b). Such embodiments comprise contacting the solid support-bound product of (b) with one or more of aqueous ammonia, NaOH, $K_2CO_3$, t-butylamine, and combinations thereof.

In some embodiments, the method further comprises purifying the deprotected and/or cleaved solid support-bound product of (b). In such embodiments, the method comprises purifying the deprotected and/or cleaved solid support-bound product of (b) with gel electrophoresis or reversed-phase high-performance liquid chromatography (HPLC).

In particular embodiments, the one or more nucleoside residues attached to the solid phase support comprise at least one N6-(2-Deoxy-α,β-D-erythropentofuranosyl)-2,6-diamino-4-hydroxy-5-formamidopyrimidine (Fapy·dG) moiety:

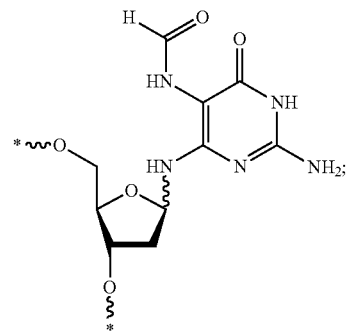 [SMILES: *OC[C@H]1O[C@@H](Nc2nc(N)[nH]c(=O)c2NC=O)C[C@H]1O*]

wherein * denotes a point of attachment of the Fapy·dG moiety to one or more other nucleosides.

In other embodiments, the one or more nucleoside residues attached to the solid phase support comprise at least one N4-(2-Deoxy-α,β-D-erythropentofuranosyl)-4,6-diamino-5-formamidopyrimidine (Fapy·dA) moiety:

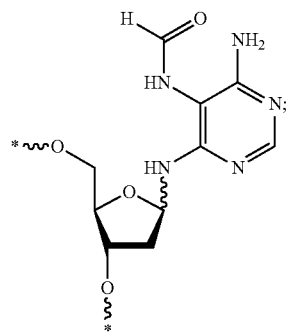 [SMILES: *OC[C@H]1O[C@@H](Nc2ncnc(N)c2NC=O)C[C@H]1O*]

wherein * denotes a point of attachment of the Fapy·dA moiety to one or more other nucleosides.

In some embodiments, the synthesized oligonucleotide comprises at least one Fapy·dG moiety. In other embodiments, the synthesized oligonucleotide comprises at least one Fapy·dA moiety.

In particular embodiments, the synthesized oligonucleotide comprises one or more nucleoside selected from the group consisting of adenosine (A), guanosine (G), cytidine (C), and thymidine (T). In yet more particular embodiments, the synthesized oligonucleotide is selected from the group consisting of:

| | |
|---|---|
| 5'-$d(T_{10}×T_4)$ SEQ ID NO: 1 | 17 |
| 5'-$d$(TTT AGG CGT GGT GAT GCT GTG TGC TAT GGT) SEQ ID NO: 2 | 18 |
| 5'-$d$(GCT GAT GCG X) SEQ ID NO: 3 | 19 |
| 5'-$d$(CGC AXC GCT GCG) SEQ ID NO: 4 | 20 |
| 5'-$d$(GTG CXT GTT TGT) SEQ ID NO: 5 | 21 |
| 5'-$d$(AAC CXG AGG CCC) SEQ ID NO: 6 | 22 |

| | |
|---|---|
| 5'-d(AAC CGG AXG CCC) SEQ ID NO: 7 | 23 |
| 5'-d(GGA AGC AAT XGT ACG G) SEQ ID NO: 8 | 24 |
| 5'-d(CCG ACX TCG CAT CAG C) SEQ ID NO: 13 | 25 |
| 5'-d(AGG GCG GTG TXG GAA GAG GGA) SEQ ID NO: 9 | 26 |
| 5'-d(AAC CXG AGG CCC ATC CTC AC) SEQ ID NO: 10 | 27 |
| 5'-d(GTG CXT GTT TGT GCC TGT CC) SEQ ID NO: 11 | 28 |
| 5'-d(TGT TCA TCA TGG GTC XTC GGT ATA TCC CAT) SEQ ID NO: 12 | 29 | x=Fapy·Dg.

In yet more particular embodiments, the presently disclosed subject matter provides a method for synthesizing an oligonucleotide, the method comprising: (a) providing a nucleoside phosphoramidite comprising a 2'-deoxyribose moiety having a 3'-hydroxyl position and a 5'-hydroxyl position, wherein the nucleoside phosphoramidite has a dimethoxytrityl protecting group at the 3'-hydroxyl position and a phosphoramidite moiety at the 5'-hydroxyl position; (b) detritylating the nucleoside phosphoramidite having a dimethoxytrityl protecting group at the 3'-hydroxyl position of (a) to form a detritylated nucleoside phosphoramidite; (c) contacting the detritylated nucleoside phosphoramidite of (b) with an activator to form an activated detritylated nucleoside phosphoramidite; (d) contacting the activated detritylated nucleoside phosphoramidite of (c) with one or more nucleoside residues attached to a solid phase support to form a solid support-bound product; (e) contacting the solid support-bound product of (d) with an oxidizing agent to form an oxidized solid support-bound product; (f) capping the oxidized solid support-bound product of (e) to form a capped solid support-bound product; and (g) deprotecting and/or cleaving the capped solid support-bound product of (f).

In yet other embodiments, the presently disclosed subject matter provides a method for preparing N6-(2-Deoxy-α,β-D-erythropentofuranosyl)-2,6-diamino-4-hydroxy-5-formamidopyrimidine (Fapy·dG) phosphoramidite (1) as disclosed in Scheme 7 herein below:

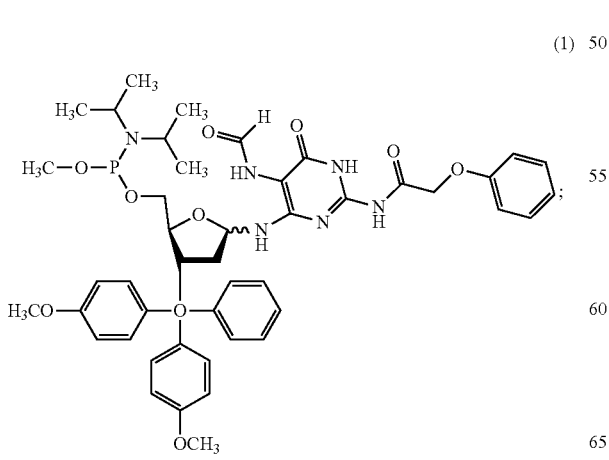

(1)

the method comprising:
(a) providing a compound 9:

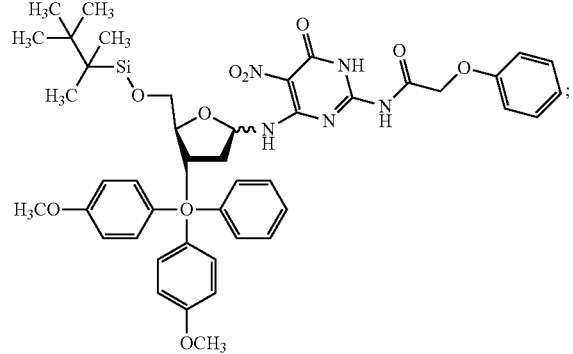

(9)

(b) contacting compound (9) with diphenylcarbamoyl chloride, followed by triethylamine (Et$_3$N) to yield compound (14):

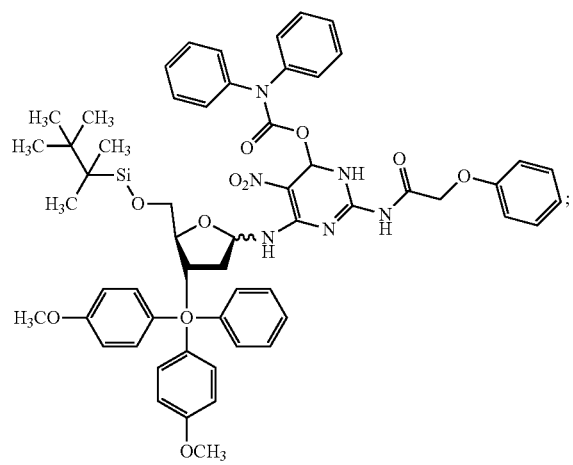

(14)

(c) contacting compound (14) with Et$_3$N·3HF to yield compound (15):

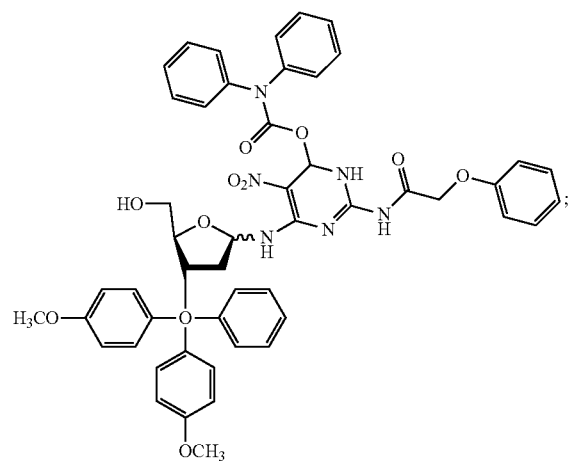

(15)

(d) contacting compound (15) with N, N-diisopropylethylamine (DIPEA), followed by diisopropylmethylphosphanamidic chloride to yield compound (16):

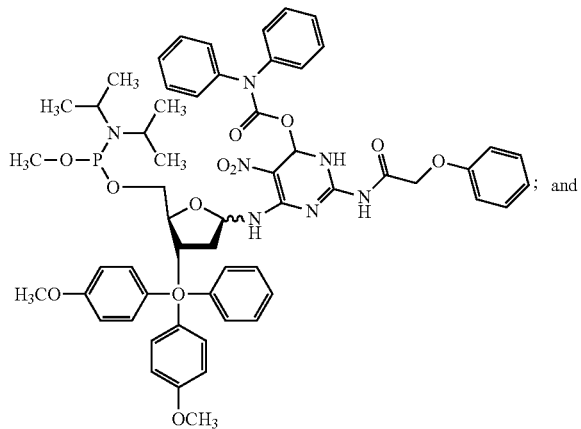

(16)

(e) contacting compound (16) with:
   (i) DIPEA and palladium on carbon; and
   (ii) pressurizing with $H_2$; and
   (iii) followed by contacting with pivalic formic anhydride to form (1).

In even yet other embodiments, the presently disclosed subject matter provides a compound comprising the following structure:

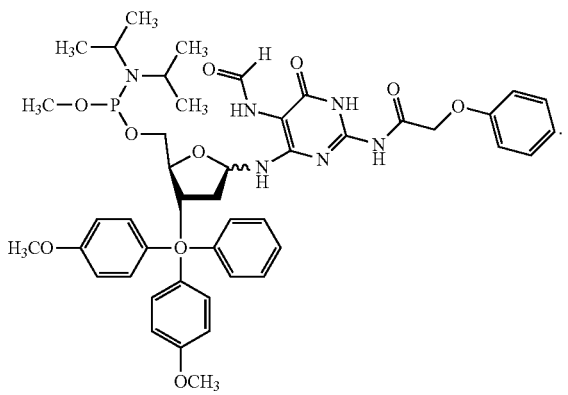

(1)

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Solid-Phase Synthesis of Oligonucleotides Containing the N6-(2-Deoxy-α,β-D-erythropentofuranosyl)-2,6-diamino-4-hydroxy-5-formamidopyrimidine (Fapy·dG) Oxidative Damage Product Derived from 2'-Deoxyguanosine 1.1 Overview N6-(2-Deoxy-α,β-D-erythropentofuranosyl)-2,6-diamino-4-hydroxy-5-formamidopyrimidine (Fapy·dG) is produced from 2'-deoxyguanosine under oxidizing conditions from a common intermediate that leads to 7,8-dihydro-8-oxo-2'-deoxyguanosine (8-OxodGuo). The impact of Fapy·dG on DNA structure and function is much less well understood than that of 8-OxodGuo. This lack of understanding is largely due to the significantly greater difficulty in synthesizing oligonucleotides containing Fapy·dG than 8-OxodGuo. The presently disclosed subject matter provides a synthetic approach for preparing oligonucleotides containing Fapy·dG that will facilitate intensive studies of this lesion in DNA. A variety of oligonucleotides as long as 30 nucleotides are synthesized. It is thought that the chemistry described herein will provide an impetus for a wide range of studies involving Fapy·dG.

1.2 Background

DNA oxidation plays a prominent role in the etiology and treatment of diseases, as well as ageing. Consequently, how individual damaged nucleotides are recognized by polymerases, glycosylases and other proteins involved in DNA repair is fundamentally important. Cadet et al., 2017; Dizdaroglu, 2015. In addition, recent evidence suggests that damaged nucleotides may also play a role in regulating transcription. Fleming et al., 2017; Redstone et al., 2019; Zhu et al., 2018; Pan et al., 2016; and Allgayer et al., 2016. As the most readily oxidized native nucleotide, 2'-deoxyguanosine modifications have been of significant interest. Shafirovich and Geacintov, 2017. Of these, 7,8-dihydro-8-oxo-T-deoxyguanosine (8-OxodGuo), the two-electron oxidation product resulting from formal hydroxyl radical addition to the C8-position of dG ($C8_{Add}$, Scheme 1) is the most well studied lesion. Amente et al., 2019; Freudenthal et al., 2015; Menoni et al., 2012; van der Kemp et al., 2019; and McCulloch et al., 2009.

The corresponding 2,6-diamino-4-hydroxy-5-formamidopyrimidine derived from dG (Fapy·dG) is believed to also arise from $C8_{Add}$, and under some conditions is produced in greater amounts than 8-OxodGuo. Greenberg, 2012. The effects of Fapy·dG, however, on biochemical and cellular processes, as well as nucleic acid structure, are less well understood. Obtaining knowledge about the effects of Fapy·dG is hindered due to the relative difficultly in synthesizing oligonucleotides containing this lesion. The presently disclosed subject matter, in part, provides a significant advance in synthesizing oligonucleotides containing Fapy·dG that will facilitate studies on this important DNA modification.

Although formed as a consequence of oxidative stress, Fapy·dG is at the same oxidation state as dG. In fact, cyclization and dehydration of Fapy·dG is a possible biosynthetic pathway to the native nucleotide. Becker et al., 2016. Fapy·dG is believed to result from one electron reduction of $C8_{Add}$; whereas 8-OxodGuo formation requires a second oxidation step (Scheme 1). Dizdaroglu et al., 2008. The dependence of the relative levels of Fapy·dG and 8-OxodGuo on the environment in which $C8_{Add}$ is produced is generally consistent with this mechanism. Jaruga et al., 2008; Douki et al., 1997; Pouget et al., 2002; Cadet and Wagner, 2013; Xue and Greenberg, 2007.

8-OxodGuo formation is favored under $O_2$ rich conditions, but Fapy·dG is detected at higher levels in cells. The Scheme 1.

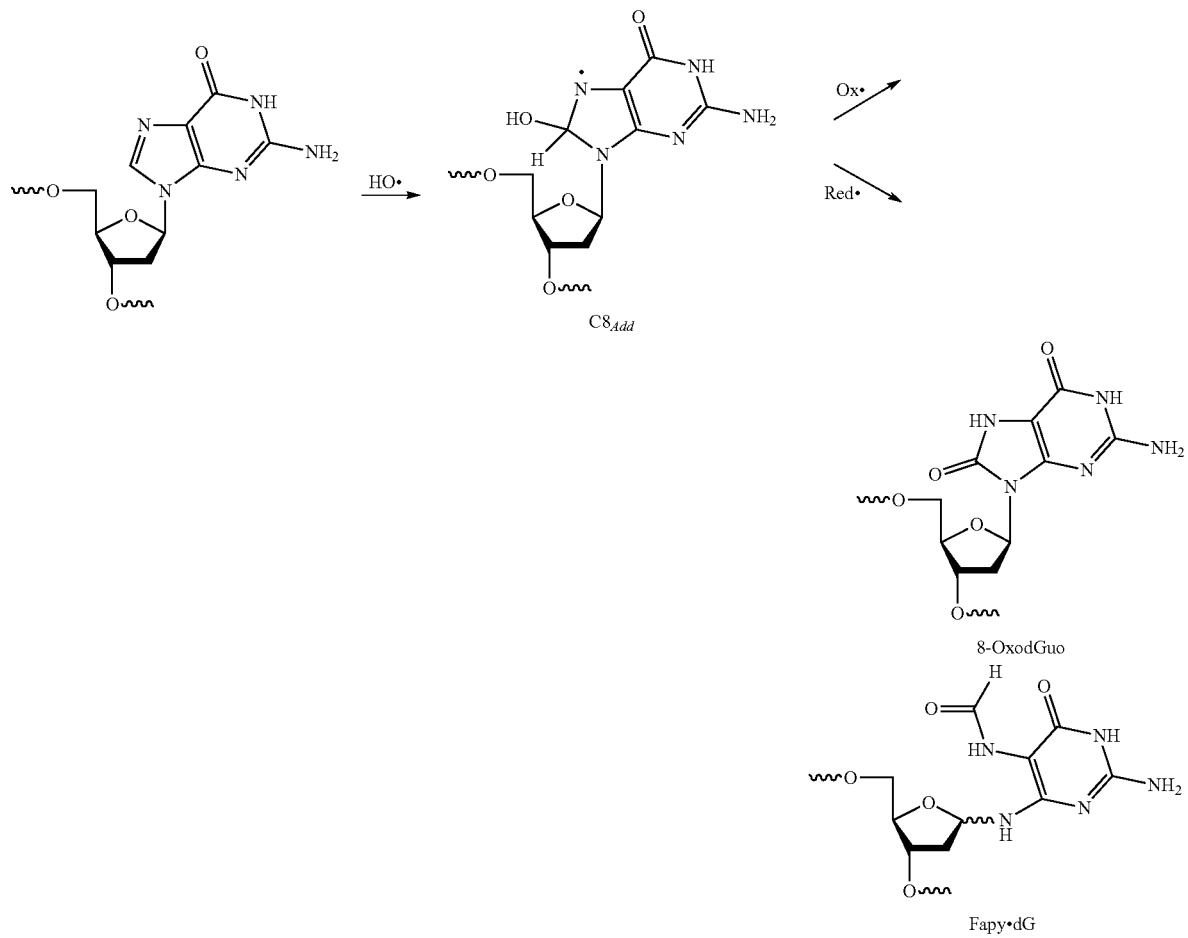

preferential formation of Fapy·dG over 8-OxodGuo in cells is attributed to lower $O_2$ concentration than in a test tube and the presence of reducing agents in this environment. A recent report, however, described Fapy·dG formation in the test tube to require exhaustive $O_2$ depletion in solution. Alshykhly et al., 2015. Fapy·dG and 8-OxodGuo have also been proposed as part of complex lesions in DNA as a result of their formation of nucleotide peroxyl radicals. Douki et al., 2002; Bergeron et al., 2010. The subsequent partitioning of the peroxyl radical adduct(s), however, is expected to follow the same dependence as $C8_{Add}$ on $O_2$.

Inferential support for the biological significance of Fapy·dG is that not only is it recognized by the proteins involved in repairing guanine oxidation (GO) products, but it is repaired in a manner to guard against introducing mutations. Shafirovich and Geacintov, 2017.

For instance, the bacterial (Fpg) and human glycosylases (hOGG1) that selectively recognize 8-OxodGuo opposite dC versus dA act similarly on Fapy·dG. Fpg hydrolyzes the glycosidic bond of the lesion in a Fapy·dG:dC base pair almost 20-times more efficiently than when opposite dA. Wiederholt et al., 2003. hOGG1 is even more selective, discriminating against a Fapy·dG:dA base pair by more than 40-fold. Krishnamurthy et al., 2008. The bacterial glycosylase, MutY, incises a mismatched dA opposite Fapy·dG more rapidly than from a dG:dA mispair, but 4-fold more slowly than from a duplex containing 8-OxodGuo:dA. Wiederholt et al., 2003; Chmiel et al., 2003; and Porello et al., 1998.

The relevance of a Fapy·dG:dA base pair is born-out by mutagenesis studies. Fapy·dG bypass in *E. coli*, as well as mammalian cells, gives rise to G to T transversions. The frequency of dA misincorporation opposite Fapy·dG was consistently lower in *E. coli* than when single-stranded plasmids containing 8-OxodGuo were replicated. Patro et al., 2007. In mammalian cells (COS-7, HEK293T), Fapy·dG mutagenicity resulting from dA misincorporation, was much more comparable to that of 8-OxodGuo, and in some instances was greater. Kalam et al., 2006; Pande et al., 2015. Insight into the structural basis for FapydG mutagenicity and recognition by repair enzymes have been limited to a carbacyclic analogue (carba-Fapy·dG, see immediately herein below), due to the difficulty in synthesizing oligonucleotides containing Fapy·dG. Gehrke et al., 2013; Coste et al., 2004. FapydG recognition by translesion synthesis polymerases and other repair enzymes is also not well understood. This too could be due to synthetic limitations that make it difficult for many investigators to obtain oligonucleotide substrates containing Fapy·dG.

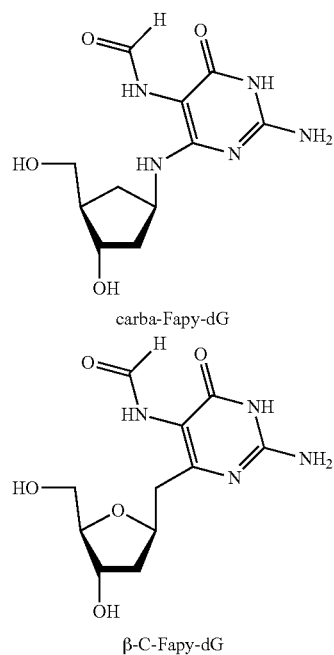

carba-Fapy-dG

β-C-Fapy-dG

Solid-phase synthesis of oligonucleotides containing Fapy·dG is challenging due to the availability of the N6-lone pair electrons, which facilitates reversible ring opening of the deoxyribose ring (Scheme 2). Berger and Cadet, 1985.

Scheme 2.

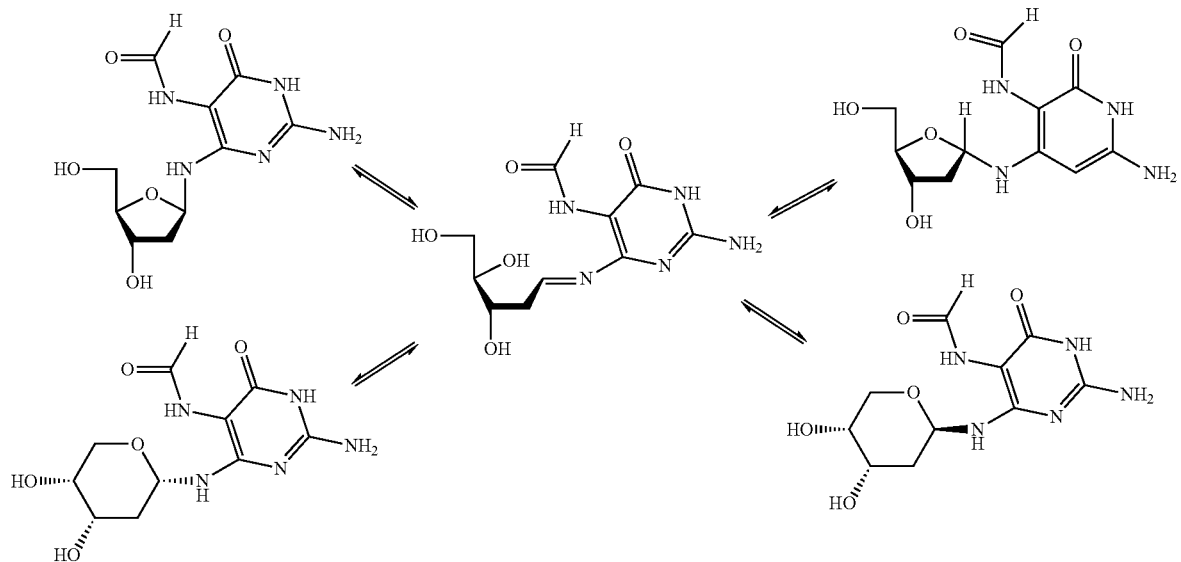

This reversible ring opening results in epimerization and Fapy·dG exists as a mixture of α- and β-anomers in duplex DNA. Patro et al., 2004. When present as a nucleoside, exposure of the primary hydroxyl results in preferential isomerization to the pyranose form of Fapy·dG. Possible formation of the pyranose isomer within DNA was a major consideration when designing a method for synthesizing oligonucleotides containing Fapy·dG.

Isomerization is avoided by synthesizing carbacyclic (carba-Fapy·dG) or C-nucleoside (β-C Fapy·dG) analogues, but these model compounds may not completely recapitulate the structure of the native lesion. Burgdorf and Carell, 2002; Delaney and Greenberg, 2002. Rizzo used 3'- to 5'-solid-phase phosphoramidite chemistry to synthesize oligonucleotides containing N5-alkylated Fapy·dG variants. Christov et al., 2008; Christov et al., 2009.

Isomerization to the pyranose form during acidic deprotection of the primary hydroxyl group was minimized by decreasing the detritylation reaction time. Oligonucleotides containing the pyranose isomer were removed by reverse-phase HPLC and in some instances this additional purification step was not reported. Another strategy involved post-synthetic reduction of a 5-nitro group, followed by formylation. Lukin et al., 2011. The strong electron withdrawing nitro group prevents isomerization to the pyranose isomer when the 5'-hydroxyl group is revealed during oligonucleotide synthesis. A strategy previously developed utilizing dinucleotide phosphoramidites to prevent isomerization to the pyranose isomer also made use of the 5-nitro substituent. Haraguchi et al., 2002; Haraguchi et al., 2001; Jiang et al., 2005. This strategy provided oligonucleotides without any concern for pyranose formation or the need for additional purification. The syntheses of the dinucleotides, however, were lengthy, coupling yields on solid-phase support were modest (50-70%), and/or required double-coupling of the Fapy·dG phosphoramidite. Finally, the ability to synthesize any oligonucleotide sequence required preparing four dinucleotides, of which only two were reported.

2. Materials and Methods 2.1 Materials

Triethylamine, pyridine, diisopropylamine, t-butylamine, 2,6-lutidine, ethyl acetate and dichloromethane were distilled from CaH$_2$ under Ar. Methanol was dried over molecular sieves 3 Å and distilled under Ar. THF was distilled from Na under Ar. Pivalic anhydride was distilled under vacuum. All other reagents were purchased from commercial sources and used without further purification unless otherwise stated.

Nuclear magnetic resonance spectra were acquired on Bruker 400 MHz for $^1$H, 101 MHz for $^{31}$P and 125 MHz for $^{13}$C. HR ESI mass spectra were recorded on a Waters Acquity/Xevo-G2 UPLC-MS system in positive mode. MALDI-TOF spectra were recorded on a Bruker AutoFlex III MALDI-TOF/TOF mass spectrometry in negative mode. Oligonucleotide synthesis was carried out on an ABI-394 synthesizer.

N-Phenoxyacetyl protected 3'-dimethoxytrityl 5'β-cyanoethyl 2'-deoxyadenosine phosphoramidite (dAPac) was synthesized as previously described. Haraguchi et al., 2002. The requisite "reverse" 5'β-cyanoethyl phosphoramidites for thymidine (dT) and N,N-dimethylformamidine 2'-deoxyguanosine (dGdmf) were obtained from Glen Research. Reverse phosphoramidite, N-acetyl 2'-deoxycytidine (dCAc), as well as Universal UnyLinker™ Support were purchased from Chemgenes. See Ravikumar et al., 2008. All other commercially available oligonucleotide synthesis reagents were purchased from Glen Research. HP Cyano RediSep Rf gold chromatography column (15.5 g) was purchased from Teledyne ISCO.

2.2 Experimental Methods

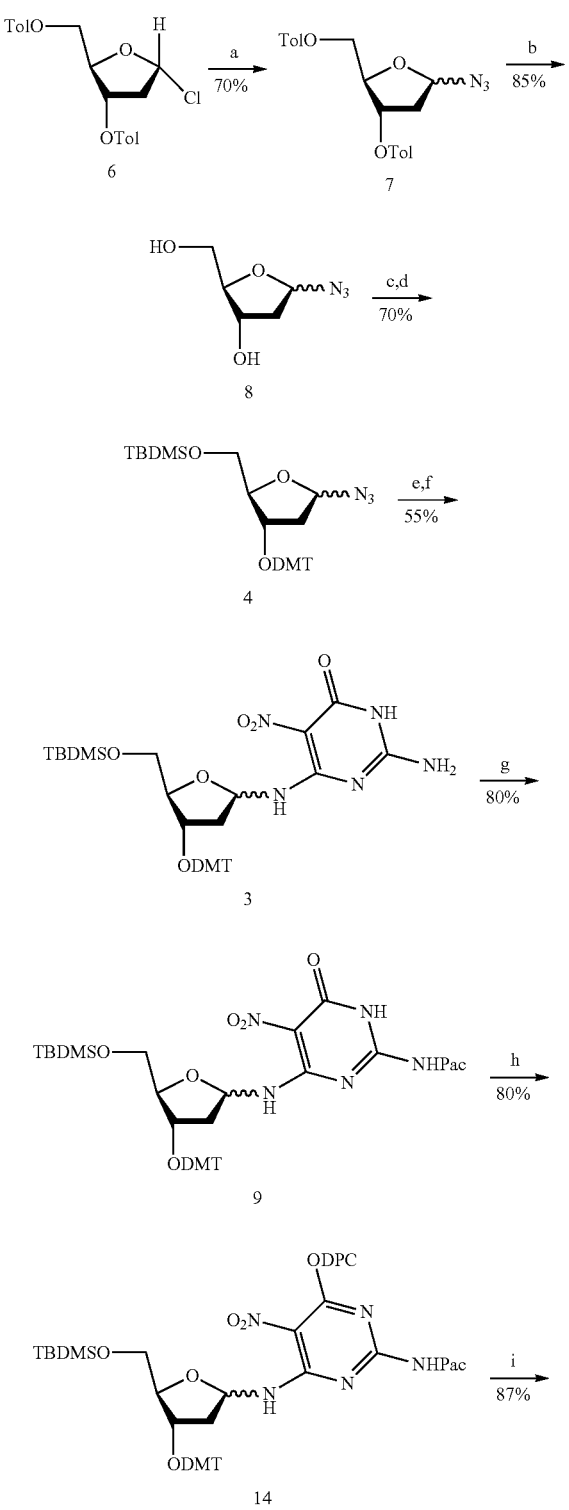

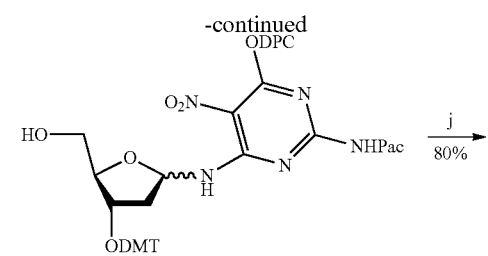

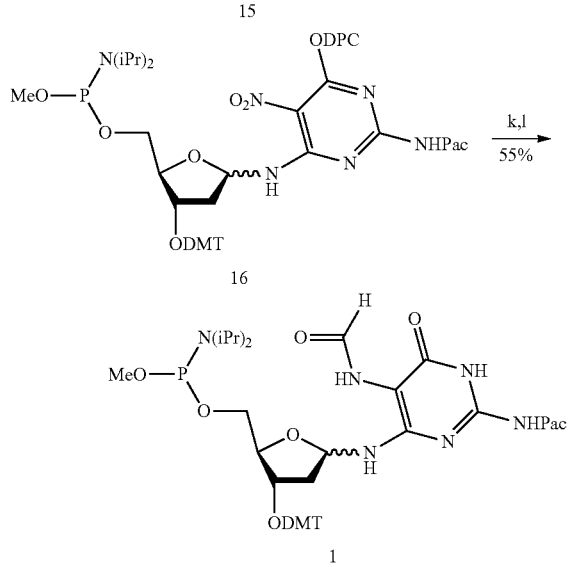

Key: a) BF$_3$·Et$_2$O, TMSN$_3$, CH$_2$Cl$_2$ b) NaOMe, MeOH c) TBDMSCl, pyridine d) DMTCl, pyridine e) Pd/CacO$_3$, H$_2$, EtOH f) DIPEA, 5, EtOH g) Phenoxyacetic acid, PyBOP, DIPEA, CH$_2$Cl$_2$ h) Diphenylcarbamoyl chloride, Et$_3$N, pyridine i) Et$_3$N·3HF, THF j) N,N-Diisopropylmethylphosphonamidic chloride, DIPEA, CH$_2$Cl$_2$ k) Pd/C, H$_2$, DIPEA, ethyl acetate l) pivalic formic anyhydride, ethyl acetate Key: a) BF$_3$·Et$_2$O, TMSN$_3$, CH$_2$Cl$_2$ b) NaOMe, MeOH c) TBDMSCl, pyridine d) DMTCl, pyridine e) Pd/CacO$_3$, H$_2$, EtOH f) DIPEA, 5, EtOH g) Phenoxyacetic acid, PyBOP, DIPEA, CH$_2$Cl$_2$ h) Diphenylcarbamoyl chloride, Et$_3$N, pyridine i) Et$_3$N·3HF, THF j) N,N-Diisopropylmethylphosphonamidic chloride, DIPEA, CH$_2$Cl$_2$ k) Pd/C, H$_2$, DIPEA, ethyl acetate l) pivalic formic anhydride, ethyl acetate
Scheme 7. Synthetic Route for Fapy·dG Phosphoramidite.

Preparation of 5 (see Babaoglu et al., 2004). H$_2$SO$_4$ (24 mL) and fuming HNO$_3$ (90%, 24 mL) were mixed at 0° C. 2-Amino-6-chloro-1H-pyrimidin-4-one (4 g) was added in small portions. A significant exothermic reaction was observed when the pyrimidine was added. The rate of addition of the nucleobase should be controlled to maintain the temperature of the reaction mixture below 40° C. After 3 h, the reaction mixture was poured into ice. The precipitate was filtered and washed with H$_2$O several times until neutral. The filter cake was then washed with ice-cold ethanol, ether and then dried under vacuum to afford 5 (2.2 g, 90%) as a yellowish solid. The crude material was used with no further purification. $^1$H NMR (400 MHz, DMSO) δ 12.0 (br s, 1H), 8.49 (br s, 1H), 7.07 (br s, 1H).

Preparation of 3. Compound 3 was prepared in 55% yield (10.5 g) from 4 (8.6 g) as previously described (Haraguchi and Greenberg, 2001).

Preparation of 4. Compound 4 was prepared in 70% yield (8.9 g) from 8 (3.5 g) as previously described (Haraguchi and Greenberg, 2001), with the exception that crude 5-silylated azido intermediate was directly used for tritylation without any purification.

Preparation of 9. Compound 9 was prepared in 80% yield (5.5 g) from 3 (5.8 g) as previously described (Haraguchi and Greenberg, 2001), with the exception that chromatographic purification was carried out using 2%-5% acetone in DCM.

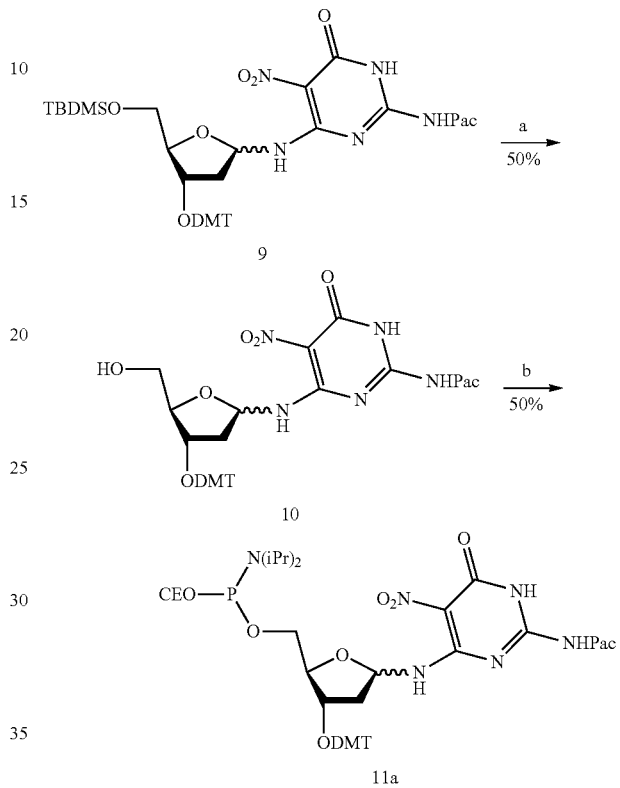

Key: a) Et$_3$N·3HF, THF b) 2-Cyanoethyl-N,N,N',N'-tetraisopropylphosphordiamidite, S-ethyltetrazole, DIPEA, CH$_2$Cl$_2$ Preparation of 10. Compound 9 (400 mg, 0.48 mmol) was dissolved in THF (6 mL). Et$_3$N·3HF (770 mg, 4.8 mmol) was added and the reaction was stirred at room temperature overnight. The mixture was diluted with ethyl acetate, washed with saturated NaHCO$_3$ and then brine. The organic layer was collected, dried over Na$_2$SO$_4$ and evaporated to dryness under vacuum. The residue was chromatographed on silica gel (10%-20% acetone in DCM) to give a diastereomeric mixture of 10 (173 mg, 50%) as a foam. The $^1$H NMR spectrum of the isomers was consistent with the reported data (Haraguchi and Greenberg, 2001).

Preparation of 11a. Compound 10 (100 mg, 0.14 mmol) was azeotropically dried with toluene (2×10 mL) and dried in vacuo for 2 h before it was dissolved DCM (1 mL) at 0° C. DIPEA (36 mg, 0.28 mmol) was then added, followed by 2-cyanoethyl N, N, N', N'-tetraisopropylphosphorodiamidite (84.4 mg, 0.28 mmol) and 5-ethylthio-1H-tetrazole (20 mg, 0.14 mmol). After 10 min, the reaction was brought to room temperature. The reaction was stirred for 3 h and then diluted with DCM (2 mL). The reaction mixture was washed with 5% NaHCO$_3$, brine, dried over Na$_2$SO$_4$ and evaporated to dryness under vacuum. The residue was chromatographed on silica gel (DCM/EtOAc=3:1) to give 11a (66 mg, 50%) as a foam. $^1$H NMR (400 MHz, CDCl$_3$): δ 10.04-10.07 (m, 1H), 7.46-7.47 (m, 1H), 7.20-7.40 (m, 10H), 7.03-7.11 (m, 1H), 6.05-6.18 (m, 1H), 4.67 (s, 2H), 4.33-4.35 (m, 1H), 4.20-4.27 (m, 1H), 3.78 (s, 6H), 3.64-3.72 (m, 3H), 3.42-

3.54 (m, 4H), 2.47-2.64 (m, 2H), 1.02-1.15 (m, 14H). $^{31}$P NMR (162 MHz, CDCl$_3$): δ 149.6, 148.6.

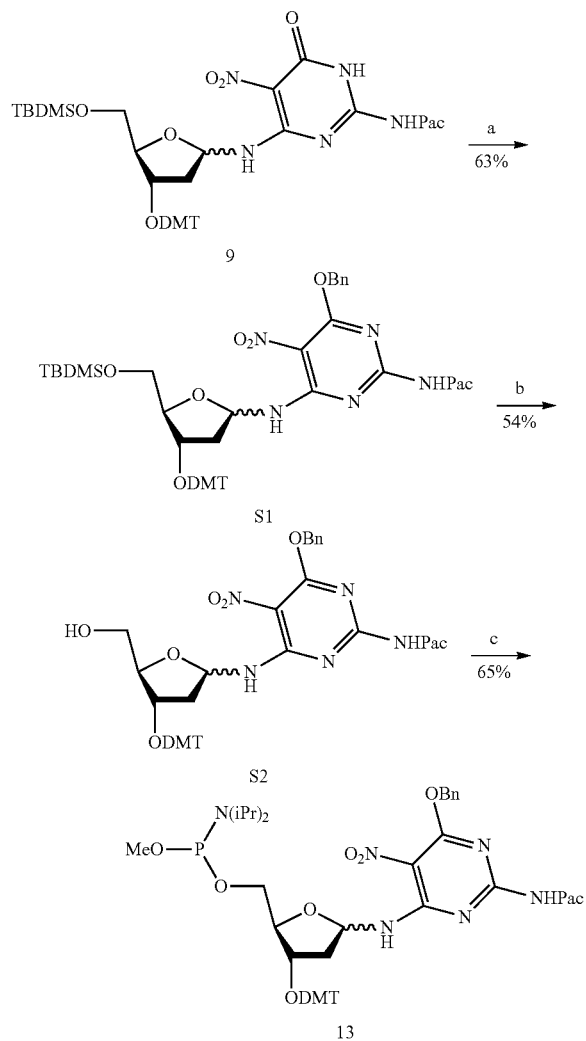

Key: a) BnOH, PPh$_3$, DEAD, THF b) Et$_3$N·3HF, THF
c) N,N-Diisopropylmethylphosphonamidic chloride, DIPEA, CH$_2$Cl$_2$ Subsequently, benzyl alcohol (125 mg, 1.2 mmol) was added dropwise, followed by diethyl azodicarboxylate (165 mg, 0.9 mmol). The reaction was stirred at 25° C. overnight and evaporated to dryness under vacuum. The residue was chromatographed on silica gel (15%-20% EtOAc in Hexane) to afford an anomeric mixture (350 mg, 63%) as a white solid. (The $^1$H NMR integration of the anomeric mixture follows. The integration is reported such that a single proton for the major anomer is normalized to 1)$^1$H NMR (400 MHz, CDCl$_3$): δ 9.14 (d, J=8.4 Hz, 1H), 8.58 (d, J=8.4 Hz, 0.35H), 8.48 (br s, 1H), 6.81-7.48 (m, 31H), 6.27 (m, 0.35H), 6.11 (t, J=7.2 Hz, 1H), 5.58 (s, 2.7H), 4.80-4.90 (m, 2.7H), 4.32-4.33 (m, 1.35H), 4.15-4.28 (m, 1.35H), 3.96 (m, 0.35H), 3.77 (d, J=2.4 Hz, 9.5H), 3.28-3.48 (m, 2.7H), 2.03 (m, 1H), 0.78 (m, 12.1H), −0.09 (d, J=1.2 Hz, 8.1H).

Preparation of S2. Compound S1 (320 mg, 0.34 mmol) was azeotropically dried with toluene/DCM (1:1, 2×2 mL) and dissolved in THF (3 mL). Et$_3$N·3HF (550 mg, 3.4 mmol) was added and stirred at 25° C. overnight. The mixture was diluted with ethyl acetate, washed with saturated NaHCO$_3$, brine, dried over Na$_2$SO$_4$ and evaporated to dryness under vacuum. The residue was purified by flash chromatography (Hexane/EtOAc=3:1-1:1) to give two isomers of S2 (160 mg, more polar isomer:less polar isomer=5:2, 54%) as a foam; less polar anomer $^1$H NMR (CDCl$_3$) δ 8.76 (m, 1H), 8.59 (br s, 1H), 6.72-7.35 (m, 23H), 6.15-6.19 (m, 1H), 5.47 (s, 2H), 4.76-4.79 (m, 2H), 4.39 (s, 1H), 4.23-4.24 (m, 1H), 3.84 (s, 1H), 3.68 (s, 6H), 3.09-3.33 (m, 2H); more polar anomer $^1$H NMR (CDCl$_3$) δ 9.16 (m, 1H), 8.57 (br s, 1H), 6.94-7.47 (m, 23H), 6.16 (t, J=6.8 Hz, 1H), 5.55 (s, 2H), 4.75-4.78 (m, 2H), 4.49 (s, 1H), 4.30 (s, 1H), 4.28 (s, 1H), 3.76 (s, 6H), 3.17-3.48 (m, 2H), 1.79-1.92 (m, 2H). HRMS (ESI-TOF) m/z [M+Na]+ calcd. for C$_{45}$H$_{43}$N$_5$NaO$_{10}$ 836.2902, found 836.2889 (more polar product).

Preparation of 13. The major isomer of S2 (80 mg, 0.1 mmol) was azeotropically dried with toluene (2×10 mL) and dried under vacuum for 2 h before it was dissolved DCM (2 mL) at 0° C. DIPEA (64 mg, 0.5 mmol) was then added, followed by diisopropylmethylphosphonamidic chloride (40 mg, 0.2 mmol). After 10 min, the reaction was brought to room temperature. The reaction was stirred for 3 h then diluted with DCM (2 mL). The resulting solution was washed with 5% NaHCO$_3$, brine, dried over Na$_2$SO$_4$ and evaporated to dryness under vacuum. The residue was purified by flash chromatography (Hexane/EtOAc=3:1) to give 13 (60 mg, 65%) as a foam. $^1$H NMR (400 MHz, CDCl$_3$): δ 9.16 (m, 1H), 8.82 (br s, 1H), 6.85-7.50 (m, 23H), 6.16 (m, 1H), 5.55 (d, J=2.4 Hz, 2H), 5.04-5.09 (m, 2H), 4.46 (S, 1H), 4.34 (s, 1H), 4.28 (s, 1H), 3.75 (s, 6H), 3.38-3.43 (m, 2H), 3.19 (dd, J1=12 Hz, J2=0.8 Hz, 3H), 0.95-1.08 (m, 14H). $^{31}$P NMR (162 MHz, CDCl$_3$): δ 149.0, 148.8.

Preparation of 7 (Bag et al., 2013) Hoffer's chloro sugar (45) (6, 10 g, 25.7 mmol) was suspended in DCM (50 mL) added with BF$_3$.Et$_2$O (360 mg, 2.6 mmol) and trimethylsilyl azide (3.8 g, 31 mmol) at 0° C. After 30 min, the reaction was brought to RT and stirred for 5 h. The reaction mixture was diluted with DCM (200 mL), washed with H$_2$O, brine and dried over Na$_2$SO$_4$. The organic solution was removed by evaporation and residue containing both α- and β-anomers was directly used for next step without purification. For characterization purposes, the mixture was purified by flash chromatography (5%-10% EtOAc in Hexane) to afford 7 (9 g, α/β=3:1, 70%) as a white solid. α-anomer: $^1$H NMR (400 MHz, CDCl$_3$) δ 7.98 (d, J=8.4 Hz, 2H), 7.91 (d, J=8.4 Hz, 2H), 7.22-7.27 (m, 4H), 5.70-5.71 (m, 1H), 5.48-5.51 (m, 1H), 4.71 (m, 1H), 4.50-4.63 (m, 2H), 2.52-2.59 (m, 1H), 2.41 (d, J=3.2 Hz, 6H), 2.21-2.42 (m, 1H); β-anomer: $^1$H NMR (400 MHz, CDCl$_3$) 7.99 (d, J=8.4 Hz, 2H), 7.89 (d, J=8.4 Hz, 2H), 7.20-7.24 (m, 4H), 5.70 (t, J=5.2 Hz, 1H), 5.56-5.59 (m, 1H), 4.52-4.60 (m, 3H), 2.38-2.42 (m, 8H). The spectra of the α- and β-isomers are consistent with the reported data.

Preparation of 8 (Lukin et al, 2011; Haraguchi and Greenberg, 2001). Sodium methoxide (1.2 g, 22.7 mmol) was added to a solution of 7 (9 g, 22.7 mmol) in dry MeOH (70 mL). The reaction was stirred at 40° C. for 2 h, at which time Amberlite GC50-H+ ion exchange resin (3.5 g) was added. The reaction mixture was stirred for another 30 min at room temperature. The resin was filtered off and the solvent was removed under vacuum.

The residue was purified by flash chromatography (5%-10% MeOH in DCM) to afford 8 (3.1 g, 80%, α/β=3:2) as a white solid. $^1$H NMR (400 MHz, CDCl$_3$) δ 5.68 (dd, J=3.4, 1.0 Hz, 1H), 5.59 (t, J=4.6 Hz, 0.5H), 4.51-4.67 (m, 0.5H), 4.30-4.25 (m, 2H), 4.51-4.00 (q, J=4.0 Hz, 0.5H), 3.82-3.65

(m, 3H), 2.23-1.93 (m, 3H). The chemical shifts of β-isomers are consistent with the reported data.

Preparation of 14. Compound 9 (Haraguchi and Greenberg, 2001) (1 g, 1.2 mmol) was coevaporated with pyridine (3×3 mL) and then dissolved in pyridine (5 mL). Diphenylcarbamoyl chloride (340 mg, 1.4 mmol. 1.2 eq.) was added, followed by Et$_3$N (183 mg, 1.8 mmol) The reaction was stirred in the dark for 40 min and then partitioned into a mixture of 5% NaHCO$_3$/EtOAc (1:1, 50 mL). The organic phase was washed with brine, dried over Na$_2$SO$_4$, filtered and concentrated to dryness under vacuum. The residue was purified by flash chromatography (Hexane/EtOAc=4:1-3:1) to provide 14 as a mixture of anomers (1 g, more polar isomer/less polar isomer=5:1, 80%) as a foam. (The $^1$H NMR integration of the anomeric mixture follows. The integration is reported such that a single proton for the major anomer is normalized to 1.) $^1$H NMR (400 MHz, CDCl$_3$): δ 9.20-9.22 (d, J=8 Hz, 1H), 8.66 (br s, 1H), 6.81-7.46 (m, 35H), 6.34-6.36 (m, 0.2H), 6.17 (t, J=8 Hz, 1H), 4.77-4.79 (m, 2.4H), 4.33-4.35 (m, 1H), 4.27 (s, 1H), 3.77 (s, 8H), 3.32-3.36 (m, 2.4H), 1.93 (m, 1H), 0.78 (s, 12H), −0.09--0.06 (d, J=12 Hz, 8H). $^{13}$C-NMR (CDCl$_3$): δ 166.8, 161.6, 158.6, 157.5, 157.1, 155.3, 149.6, 145.0, 136.4, 136.2, 130.3, 130.2, 130.1, 129.8, 129.2, 128.3, 128.2, 128.1, 127.9, 126.9, 122.3, 116.9, 114.9, 114.8, 113.4, 113.3, 113.2, 88.0, 87.2, 83.2, 77.4, 77.3, 77.1, 76.8, 75.5, 68.1, 63.6, 55.2, 38.7, 31.6, 25.3, 20.7, 18.3, 1.0, −5.3, −5.6.

Preparation of 15. Compound 14 (870 mg, 0.84 mmol) was co-evaporated with toluene/DCM (1:1, 2×2 mL) and then dissolved in THF (10 mL). Et$_3$N·3HF (1.5 mL, 8.4 mmol) was added and the reaction was stirred at room temperature overnight. The mixture was diluted with ethyl acetate and was washed with saturated NaHCO$_3$, and brine. The organic layer was dried over Na$_2$SO$_4$, filtered and evaporated to dryness under vacuum. The residue was purified by flash chromatography (Hexane/EtOAc=2:1-1:1) to provide two isomers of 15 (670 mg, 87%, more polar isomer/less polar isomer=4:1) as a foam. Less polar anomer: $^1$H NMR (CDCl$_3$) δ 8.93-8.91 (d, J=8 Hz, 1H), 7.18 (br s, 1H), 6.81-7.46 (m, 28H), 6.34-6.36 (m, 1H), 4.80-4.81 (m, 2H), 4.35-4.36 (m, 1H), 4.11-4.13 (m, 1H), 3.94 (s, 6H), 3.15-3.53 (m, 2H). $^{13}$C NMR (CDCl$_3$): δ: 167.2, 161.5, 158.7, 157.4, 155.4, 149.5, 145.3, 136.5, 136.4, 130.3, 130.2, 129.8, 129.3, 128.3, 128.0, 127.0, 122.2, 116.7, 114.9, 113.3, 87.1, 86.2, 82.9, 77.5, 77.2, 76.8, 74.8, 68.2, 62.7, 55.2, 40.9, 21.1, 14.2; More polar anomer $^1$H NMR (CDCl$_3$) δ 9.23 (d, J=8 Hz, 1H), 8.77 (br s, 1H), 6.82-7.46 (m, 28H), 6.24 (t, J=7.2 Hz, 1H), 4.67-4.77 (m, 2H), 4.32 (d, J=6.8 Hz, 1H), 4.23 (s, 1H), 3.77 (s, 6H), 3.21-3.53 (m, 2H), 1.88-1.91 (m, 1H). $^{13}$C NMR (CDCl$_3$) δ: 176.0, 172.0, 166.3, 163.5, 162.5, 161.8, 160.1, 154.4, 149.7, 141.1, 140.9, 135.0, 134.9, 134.5, 133.0, 132.9, 131.8, 127.1, 121.7, 119.6, 118.2, 91.8, 87.9, 82.3, 81.9, 81.6, 80.3, 72.8, 67.5, 65.2, 60.0, 43.9, 25.8, 19.0. HRMS (ESITOF) m/z [M+Na]+ calcd. for C$_{51}$H$_{46}$N$_6$NaO$_{11}$ 941.3117, found: 941.3099 (less polar), 941.3095 (more polar).

Preparation of 16. The major isomer of compound 15 (270 mg, 0.29 mmol) was co-evaporated with toluene (2×10 mL) and dried in vacuo for 2 h before it was dissolved DCM (5 mL) at 0° C. DIPEA (185 mg, 1.5 mmol) was then added, followed by diisopropylmethylphosphonamidic chloride (110 mg, 0.53 mmol). After 10 min, the reaction was brought to room temperature and stirred for 1.5 h, at which time it was diluted with DCM (2 mL). The resulting solution was washed with 5% NaHCO$_3$ and brine, dried over Na$_2$SO$_4$, filtered and concentrated to dryness under vacuum. The residue was purified by flash chromatography (Hexane/EtOAc=2:1) to provide 16 (250 mg, 80%) as a foam. $^1$H NMR (400 MHz, CDCl$_3$): δ 9.20-9.22 (d, J=8 Hz, 1H), 6.82-7.38 (m, 28H), 6.16-6.22 (m, 1H), 4.77-4.80 (d, J=8 Hz, 2H), 4.43-4.37 (dd, J=16, 8 Hz, 1H), 4.33-4.28 (m, 1H), 3.74 (s, 6H), 3.42-3.46 (m, 2H), 3.26-3.31 (m, 3H), 1.12-1.13 (m, 14H). $^{31}$P NMR (162 MHz, CDCl$_3$): δ 149.0, 149.1. HRMS (ESI-TOF) m/z [M+H]+ calcd. for C$_{58}$H$_{63}$N$_7$O$_{12}$P 1080.4267, found: 1080.4252.

Preparation of 1. Phosphoramidite 16 (200 mg, 0.17 mmol), DIPEA (180 mg, 1.3 mmol) and 10% palladium on carbon (160 mg) in ethyl acetate (4 mL) were placed in a pressure tube. The reaction mixture was pressurized with H$_2$ and vented ten times and then stirred under H$_2$ (60 psi) for 3 h. The reaction atmosphere is exchanged with Ar by freeze-pump-thaw degassing. The solution was cooled to 0° C. Pivalic formic anhydride (50 mg, 0.36 mmol) was added and the reaction mixture was stirred at 0° C. for 1 h. The reaction mixture was diluted with 5 mL of EtOAc and centrifuged at 10000 RPM for 3 min. The solution was carefully removed and the solid was washed with 5 mL EtOAc. After centrifuging, the EtOAc solutions were combined, washed with 5% NaHCO$_3$, brine and dried over Na$_2$SO$_4$. The solution was filtered and evaporated to dryness under vacuum. The residue was purified by flash chromatography using DCM/Acetone=5:1 and 0.1% Et$_3$N until the less polar isomer eluted, then 2:1 DCM/Acetone to elute the more polar isomer to provide the individual anomers of 1 (90 mg, 55%, more polar/less polar=2:1). Note: Because of tailing, fractions eluted from the column were dilute. Column fractions (~6 mL) were concentrated to ~1 mL prior to TLC analysis. Less polar isomer: $^1$H NMR (CD$_3$CN) δ: 8.65-8.69 (m, 1H), 8.55-8.58 (m, 1H), 7.44-7.46 (m, 2H), 7.33-7.36 (m, 10H), 7.24-7.27 (m, 1H), 7.00-7.05 (m, 3H), 6.89 (d, J=8.4 Hz, 5H), 6.03-6.04 (m, 1H), 5.96 (q, J=8.4 Hz, 1H), 4.72 (s, 2H), 4.24-4.30 (m, 1H), 4.12 (m, 1H), 3.78 (s, 6H), 3.32-3.49 (m, 4H), 1.72-1.84 (m, 2H), 0.98-1.10 (m, 12H), $^{31}$P NMR (CD$_3$CN) δ: 148.92, 148.60. More polar isomer: $^1$H NMR (CD$_3$CN) δ: 7.66 (s, 0.7H), 7.46-7.51 (m, 2H), 7.30-7.40 (m, 10H), 7.21-7.26 (m, 2H), 7.00-7.05 (m, 3H), 6.87-6.90 (m, 5H), 6.36-6.41 (m, 1H), 5.93-6.01 (m, 1H), 4.79 (s, 2H), 4.19-4.31 (m, 2H), 3.77 (s, 6H), 3.32-3.51 (m, 4H), 3.21-3.27 (m, 3H), 2.76-2.84 (m, 1H), 1.69-1.81 (m, 1H), 0.98-1.12 (m, 12H). $^{31}$P NMR (CD$_3$CN) δ: 148.86, 148.64. HRMS (ESI-TOF) m/z [M+H]+ calcd. for C$_{40}$H$_{43}$N$_5$O$_{11}$P 800.2691, found: 800.2684 (less polar isomer), 800.2678 (more polar isomer). (Please note that the mass corresponds to the hydrolyzed organophosphite product)

Oligonucleotide Synthesis, Deprotection, and Characterization.

The incorporation of Fapy·dG (1) into oligonucleotides with reverse β-cyanoethyl phosphoramidites was carried out on 1 μmol scale using 4,5-dicyanoimidazole (0.25 M in acetonitrile) as activating agent. Acetonitrile solutions of phosphoramidites synthesized in our laboratory (1, dAPac) were filtered using 0.45 μm syringe filters. The coupling of 1 is extremely sensitive to water. Thus, molecular sieves were added to the solution after filtering and kept in the bottle throughout oligonucleotide synthesis. The wait time for the coupling of Fapy·dG phosphoramidite was extended to 900 s, while for other phosphoramidites the wait time was 180 s. After coupling 1, commercially available phenoxyacetic anhydride (Cap A mix) and N-methyl imidazole (Cap B mix) solutions were replaced by pivalic anhydride/2, 6-lutine/THF (1:1:8, v/v/v). Capping was carried out 60 s at all steps during oligonucleotide synthesis. t-BuOOH (1 M in toluene) was used for oxidation (40 s). Following solid phase synthesis, the methyl group was removed from the Fapy·dG phosphate triester using disodium 2-carbamoyl-2-cyanoethylene-1,1-dithiolate trihydrate (0.2 M in DMF, 0.3 mL) for 30 min at room temperature. Haraguchi et al., 2002; Haraguchi and Greenberg, 2001. The resin was then rinsed successively with MeOH, THF and $CH_2Cl_2$, vacuum dried and treated with aq. NaOH (0.1 M) at room temperature for 12 h. The deprotection time was extended to 16 h for oligonucleotides containing large numbers of dG (e.g., 28). The solution was neutralized (per pH paper) with AcOH (5% in MeOH, ~0.5 vol. of the NaOH solution), concentrated to dryness and purified using 20% denaturing polyacrylamide gel electrophoresis. Alternatively, the resin was incubated with $tBuNH_2/H_2O$ (1:3, v/v) at 40° C. for 6 h and neutralized (per pH paper) with glacial acetic acid (~0.1 vol. of the $tBuNH_2$ solution). The isolated oligonucleotides were characterized by MALDI-TOF MS or ESI-MS (FIGS. 1-13).

3. Results and Discussion 3.1 Strategic Overview

Without wishing to be bound to any one particular theory, it was thought that oligonucleotides containing Fapy·dG could be prepared via solid-phase synthesis using a (reverse) phosphoramidite in which the dimethoxytrityl protecting group was at the 3'-hydroxyl position and the 5'-hydroxyl contained the phosphoramidite (1, Scheme 3). This approach avoids exposing the 5'-hydroxyl group during oligonucleotide synthesis, preventing isomerization to the pyranose isomer. In addition, a single phosphoramidite could be used to synthesize any oligonucleotide sequence. The synthesis of the phosphoramidite takes advantage of the 5-nitro substituent to enable exposing the 5'-hydroxyl without incurring isomerization (Scheme 2). Haraguchi et al., 2002; Haraguchi and Greenberg, 2001; Jiang et al., 2005. In addition, an unusual and important aspect of this strategy includes introducing the formamide group in the presence of the phosphoramidite (2). The phosphoramidite component is usually introduced in the final step of a synthesis due to its lability. The viability of this aspect of the strategy was established by examining the compatibility of a commercially available thymidine phosphoramidite with representative hydrogenation ($Pd/CaCO_3$, $H_2$) and formylation (formic acetic anhydride) conditions used to convert the nitro group into a formamide was established prior to embarking upon the synthesis.

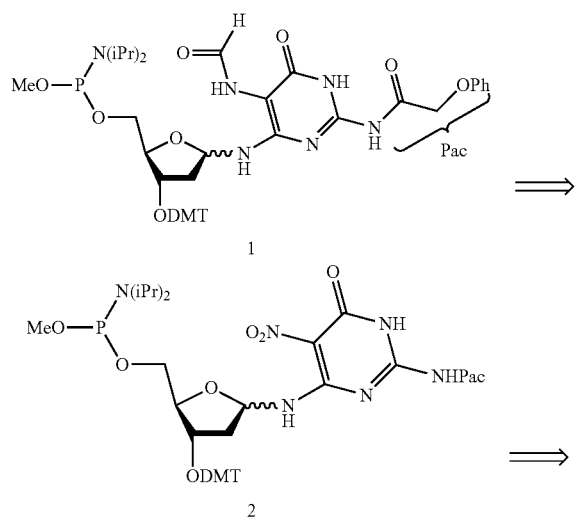

Scheme 3.

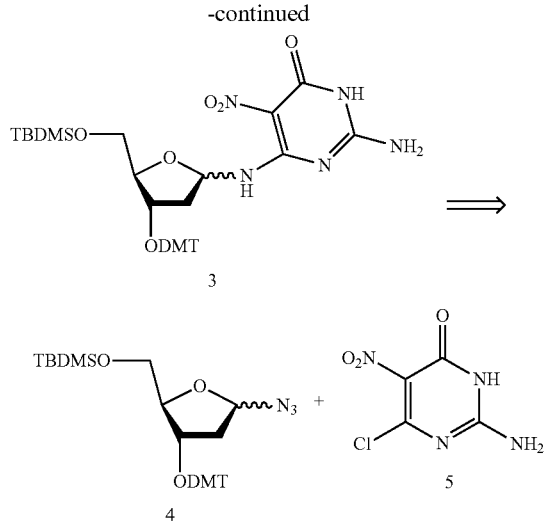

Synthesis of Phosphoramidite 1

The syntheses of dinucleotide phosphoramidites employed for preparing oligonucleotides containing Fapy·dG provided useful information for the synthesis of 1. Haraguchi et al., 2002; Haraguchi and Greenberg, 2001; Jiang et al., 2005. The presently disclosed subject matter also provided an opportunity to improve transformations that were common to the two methods. For instance, carefully controlling the temperature of the electrophilic nitration reaction provided 5 in greater yield than previously obtained (90% versus 50%). The synthesis of 4 also was improved by starting from Hoffer's sugar (6, Scheme 4), which can be prepared in large quantities. Rolland et al., 1997.

The α- and β-anomers of 7 were formed in a 3:1 ratio (a:b) and were separable. There was no advantage, however, to doing so and in practice 7 was used as a mixture. Following removal of the p-toluoyl groups, 8 was carried on to 9 via 3 as a mixture of anomers as previously described. Haraguchi et al., 2002; Haraguchi and Greenberg, 2001. Difficulty in obtaining 10 via desilylation of 9 resulted from loss of the phenoxyacetyl group (Pac) during purification. This problem was resolved by eliminating the use of triethylamine, which is often used during chromatography to guard against adventitious detritylation.

Scheme 4.

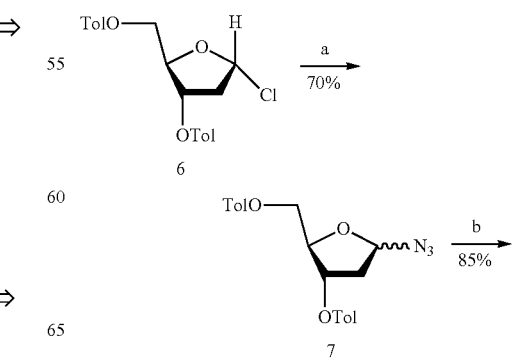

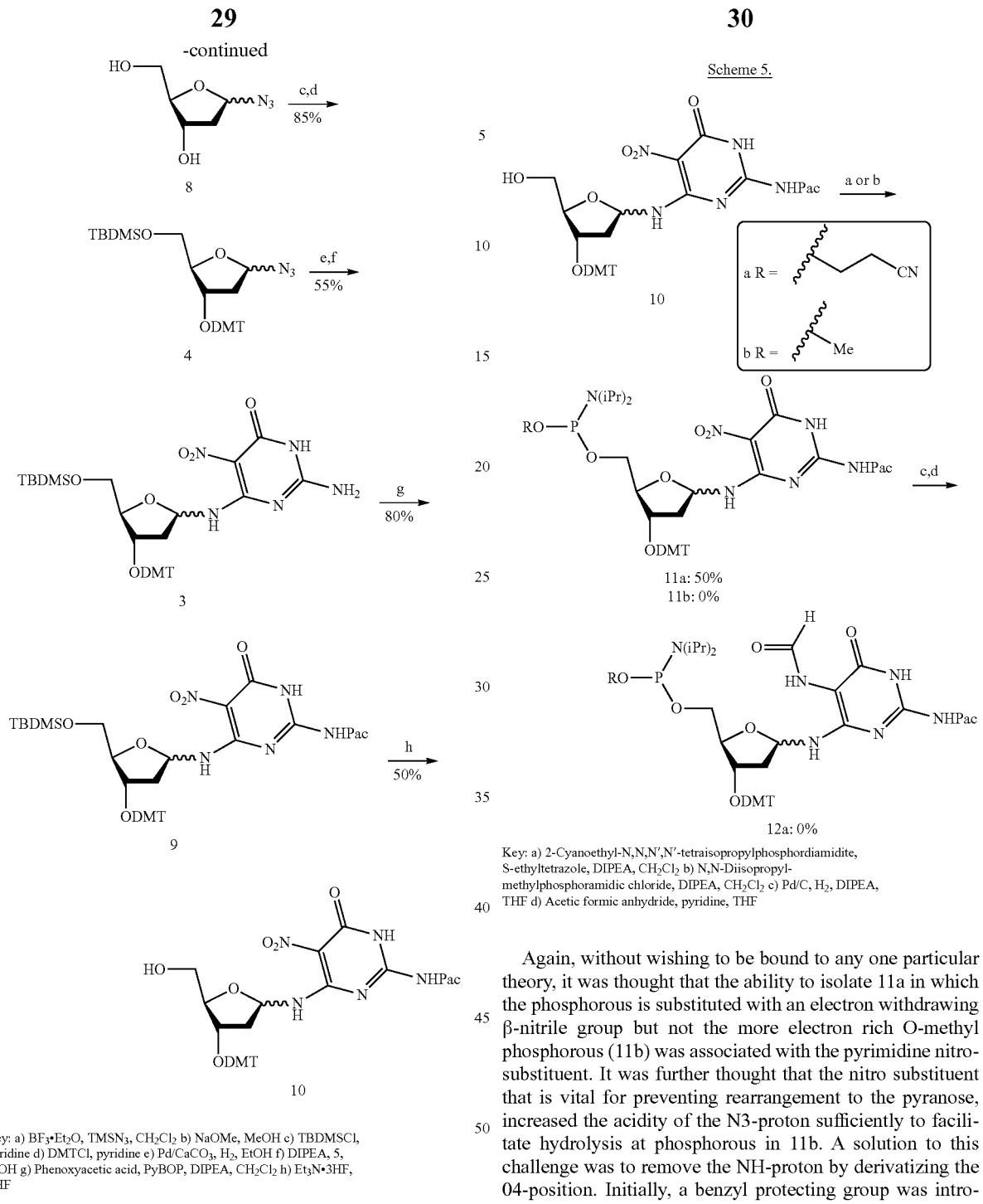

Key: a) BF₃·Et₂O, TMSN₃, CH₂Cl₂ b) NaOMe, MeOH c) TBDMSCl, pyridine d) DMTCl, pyridine e) Pd/CaCO₃, H₂, EtOH f) DIPEA, 5, EtOH g) Phenoxyacetic acid, PyBOP, DIPEA, CH₂Cl₂ h) Et₃N·3HF, THF Key: a) 2-Cyanoethyl-N,N,N',N'-tetraisopropylphosphordiamidite, S-ethyltetrazole, DIPEA, CH₂Cl₂ b) N,N-Diisopropyl-methylphosphoramidic chloride, DIPEA, CH₂Cl₂ c) Pd/C, H₂, DIPEA, THF d) Acetic formic anhydride, pyridine, THF Retrosynthetically, 10 was only 3 transformations and 2 purifications from phosphoramidite 1 (Scheme 5). Initial attempts tried to prepare the corresponding β-cyanoethyl phosphoramidite (12a, Scheme 5). Phosphitylation of 10 was accomplished in modest yield (50%). Attempts to reduce and formylate 11a, however, provided complex mixtures from which it was not possible to isolate 12a. Switching to the corresponding O-methyl phosphoramidite (11b) was less fruitful. Despite a variety of reaction conditions, 11b was contaminated with significant amounts of product(s) in which the phosphorous had undergone hydrolysis to the organophosphite.

Again, without wishing to be bound to any one particular theory, it was thought that the ability to isolate 11a in which the phosphorous is substituted with an electron withdrawing β-nitrile group but not the more electron rich O-methyl phosphorous (11b) was associated with the pyrimidine nitro-substituent. It was further thought that the nitro substituent that is vital for preventing rearrangement to the pyranose, increased the acidity of the N3-proton sufficiently to facilitate hydrolysis at phosphorous in 11b. A solution to this challenge was to remove the NH-proton by derivatizing the O4-position. Initially, a benzyl protecting group was introduced at the O4-position of 9 via a Mitsunobu reaction enroute to 13 (Scheme 6). 0-Methyl phosphoramidite formation proceeded in good yield (65%), consistent with the above hypothesis concerning the acidity of the N3-proton. Subsequent reduction and formylation, however, again yielded a complex product mixture. In addition, the benzyl group was not removed, despite experimenting with several hydrogenolysis conditions. Subsequently, the diphenyl carbamoyl (DPC) group, which has been used as an oxygen protecting group in the nitrogen heterocycles of nucleosides, was employed. Robins et al., 1996; Kamimura et al., 1984.

It was important to utilize well purified 9 to obtain good yields of 14, but the hydrophobicity of the DPC group also improved the ease of its chromatographic purification. The protected pyrimidine (14) was carried on to the nitro phosphoramidite (16), with the desilylation (15) and phosphitylation steps proceeding in good yield. Anomers of 15 were separated but only the major isomer was carried forward. The target phosphoramidite (1) was obtained, albeit in low yield (20%) when using the previously reported hydrogenation and formylation conditions. Haraguchi et al., 2002; Haraguchi and Greenberg, 2001; Jiang et al., 2005. Fortuitously, the DPC protecting group was cleaved during hydrogenation.

sensitive to the acidity of silica gel. 1, however, could be purified by conventional silica gel flash chromatography using a mixture of acetone and dichloromethane containing 0.1% triethylamine. This proved to be more reliable than an automated flash chromatography system (Combiflash Rf+) equipped with a less reactive cyano end-capped silica gel column, from which 1 could be eluted using ethyl acetate/hexane (50%-100%).

Characterization of the anomers of 1 was challenging. The overall yield of 1 from 16 was 55% and the more polar

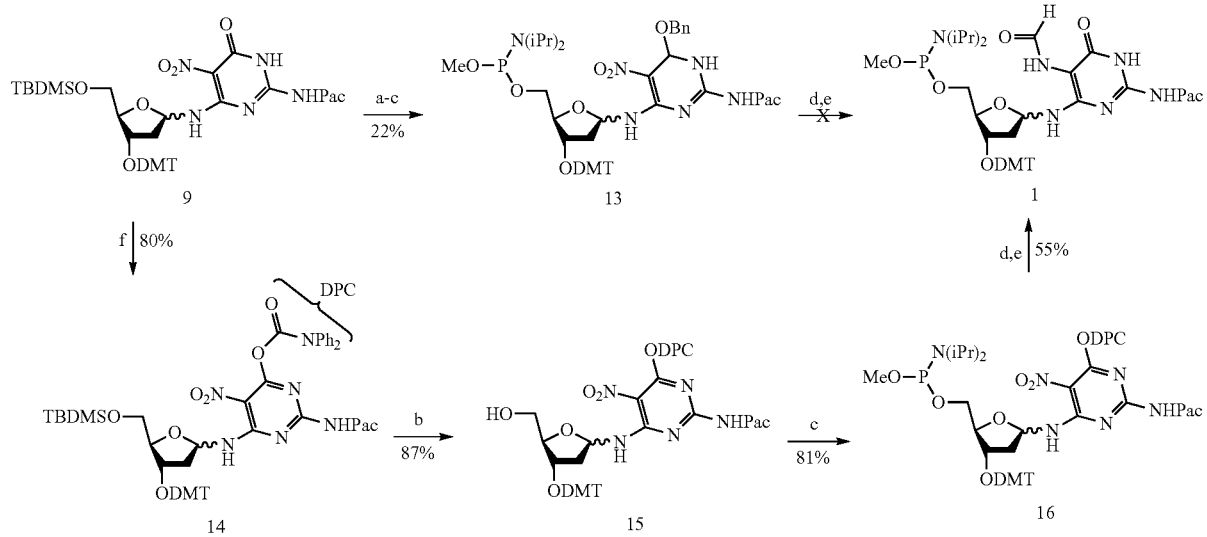

Scheme 6.

Key: a) BnOH, PPh$_3$, DEAD, THF b) Et$_3$N·3HF, THF c) N,N-Diisopropylmethylphosphonamidic chloride, DIPEA, CH$_2$Cl$_2$
d) Pd/C, H$_2$, DIPEA, ethyl acetate e) Pivalic formic anhydride, ethyl acetate f) Diphenylcarbamoyl chloride, Et$_3$N, pyridine The low yield of the one pot hydrogenation and formylation reaction is attributed to proclivity of the phosphoramidite in 1 to hydrolyze during reaction and even flash chromatography on silica gel. Hence, the difficulty of preparing acetic formic anhydride (AFA) free of acetic acid posed a significant problem when preparing 1. Cai and Guengerich, 2000. Attempts to prepare and distill pure AFA yields inconsistent results. Consequently, a variety of formylation methods were examined using model compound 9. Transfer hydrogenation and formylation using ammonium formate was unsuccessful. Pratap and Baskaran, 2001. In addition, formylation using formic acid and carbodiimide or formic acid, imidazole and oxalyl chloride did not provide the expected formamide product. The overall process was significantly improved by carrying out the hydrogenation reaction in the more hydrophobic ethyl acetate instead of THF, and substituting pivalic formic anhydride (PFA) for AFA. PFA was prepared under solvent free condition and distilled under high vacuum at 0° C. Schijf and Stevens, 1966; Vlietstra et al., 1982. The obtained anhydride product contains only trace of acids even stored for weeks. Reactions using PFA proved to be more reproducible than those with AFA. This was attributed to the greater ease of purification of PFA by distillation, as well as by deleting pyridine from the reaction mixtures. Haraguchi et al., 2002; Haraguchi and Greenburg, 2001.

These conditions provided less complicated reaction mixtures, which facilitated separation and purification of the anomers of 1. The Fapy·dG phosphoramidite (1) is very isomer was favored ~2-fold over the less polar anomer. The diagnostic formamide proton was evident in the $^1$H NMR at d 8.65-8.69 for the minor anomer, which is consistent with reported Fapyd·G derivatives and their restricted rotation. Haraguchi et al., 2002; Haraguchi et al., 2001; Jiang et al., 2005. The corresponding proton for the major, more polar isomer, however, was less evident in the $^1$H NMR spectrum. A peak accounting for ~0.7 protons was evident further upfield at d 7.66, which is close to the region at which the aromatic protons resonate.

One possibility was that the formamide proton was obscured by the large number of aromatic protons. Although mass spectrometry was consistent with its identification as an isomer of 1, confirmatory evidence for the presence of the formamide group was obtained via a $^1$H-$^{13}$C HSQC experiment, which showed the expected correlation between the formamide proton (d 7.66) and the formyl carbon signal at d158.0 A similar correlation was observed for the formamide proton of the minor anomer. (FIG. 14 and FIG. 15). If the major isomer is a-1, the upfield shift of the formyl proton in the major isomer could be attributed to shielding by the p-electrons of the aromatic ring(s). NOE experiments aimed at providing confirmation of this hypothesis, however, were ambiguous.

Synthesis and Deprotection of Oligonucleotides Containing Fapy·dG Using 1

Initial conditions for synthesizing oligonucleotides containing Fapy·dG using 1 utilized previous reports as a starting point. Haraguchi et al., 2002; Haraguchi and Greenberg, 2001. Detritylation and oxidation were carried out using trichloroacetic acid and t-BuOOH, respectively. Following coupling of 1 (0.1 M), capping with phenoxyacetic anhydride and 1-methylimidazole was replaced with pivalic anhydride/lutidine/THF. Coupling conditions of 1 using 4,5-dicyanoimidazole as activator were optimized by synthesizing a 15mer consisting of thymidines and a single Fapy·dG (see 17, FIG. 1) on a ("reverse") 3'-dimethoxytrityl thymidine support containing a succinate linkage between the 5'-hydroxyl and long chain alkylamine. On-line dimethoxytrityl cation monitoring indicated that 1 coupled from 70-80% when a 15 min reaction time was used. Separate anomers of 1 were initially used, but no difference in coupling yields was detected. Consequently, an anomeric mixture of 1 is routinely used in oligonucleotide synthesis, which also facilitates purifying the phosphoramidite. The Fapy·dG phosphoramidite (1) was much more sensitive to water in the acetonitrile used to dissolve it than commercially available phosphoramidites. To avoid hydrolysis, molecular sieves were added to the solution of 1 after filtering and were present throughout oligonucleotide synthesis. After demethylating the Fapy·dG phosphate triester with disodium 2-carbamoyl-2-cyanoethylene-1,1-dithiolate trihydrate (0.2 M, 30 min, 25° C.), Scaringe et al., 1998, 17 was deprotected and cleaved from the solid-phase support using $K_2CO_3$ (50 mM) in MeOH (25° C., 4 h). The gel purified product was characterized by ESI-MS (FIG. 1). The coupling yield of 1, as well as its synthesis was a marked improvement over the corresponding dinucleotide phosphoramidites employed previously. Haraguchi et al., 2002; Haraguchi et al., 2001; Jiang et al., 2005.

Having established satisfactory coupling conditions for 1, conditions for synthesizing oligonucleotides containing Fapy·dG and all four native nucleotides using reverse phosphoramidites were explored. To make the synthesis of Fapy·dG containing oligonucleotides accessible to the greatest number of scientists possible, it was sought to maximize the use of commercially available phosphoramidites and solid-phase synthesis supports. Reverse dT and fast deprotecting dCAc, dAPac and dGiPrac phosphoramidites are compatible with the $K_2CO_3$ conditions used to deprotect 17. Haraguchi et al., 2002; Haraguchi et al., 2001.

The latter two reverse phosphoramidites, however, are not commercially available. Reverse dimethylformamidine protected dG (dGdmf) and the respective solid-phase support are commercially available. This required establishing mutually compatible conditions for Fapy·dG and native phosphoramidite deprotection, as well as oligonucleotide cleavage from the solid-phase supports. Nucleobase deprotection conditions were tested using 17 and an oligonucleotide containing dA, dC, dG and dT (18). Oligonucleotide 18 was prepared on commercially available UnyLinker™ solid-phase synthesis support. Use of this support obviates the need for users to independently synthesize LCAA CPG containing reverse dAPac. Furthermore, any conditions sufficient for cleaving oligonucleotides from UnyLinker™ will be sufficient for removing oligonucleotides linked via the standard succinate group. dGdmf was incompletely deprotected using $K_2CO_3$ in MeOH, and remnants of the UnyLinker™ were retained at the 5'-terminus. Saturated aqueous ammonia solution in ethanol (3:1, 15° C., 10 h), which is used to deprotect oligonucleotides containing carba-Fapy·dG completely deprotected dGdmf within 18 but cleaved at Fapy·dG in 17. Gehrke et al., 2013. Oligonucleotide 17 was also cleaved at Fapy·dG when treated with concentrated $NH_4OH$ at room temperature overnight or with ammonia/methyl amine (1:1, v/v, 55° C., 1 h). Reddy et al., 1994. Fapy·dG also underwent cleavage when subjected to diisopropylethylamine (10% by volume) and β-mercaptoethanol (0.25 M) in MeOH (25° C., 2 h).

Treating 17 with t-butylamine in $H_2O$ (1:3 v/v) under the recommended conditions (60° C., 4 h) produced significant amounts of cleavage at Fapy·dG. The Glen Report, 2013. Subjecting 17 and 18 to these conditions at 40° C. for 8 h, however, provided good yields of completely deprotected oligonucleotides. The general utility of this method was demonstrated by synthesizing a series of oligonucleotides on UnyLinker™ support that contain Fapy·dG and the 4 native nucleotides (20-26) (FIG. 4-FIG. 10). In addition, 27-29 (FIG. 11-FIG. 13) were synthesized on supports containing the appropriate 5'-terminal reverse nucleoside. Fapy·dG, however, was cleaved during the deprotection when it was present at the 3'-terminus in 19. In addition, it also was determined that conditions reported for the deprotection and cleavage of oligonucleotides containing N5-methyl Fapy·dG (0.1 M NaOH, 25° C., 12 h) were compatible with Fapy·dG, the phosphoramidites employed, as well as UnyLinker™ support. Oligonucleotides 18, 19 and 26-29 were successfully obtained in comparable yields as when deprotected with t-butylamine. However, 26 required 16 h to achieve complete deprotection of the 12 dGdmf groups, while complete deprotection of 26 was achieved with t-butylamine at 40° C. for 8 h. Finally, it should be noted that the deprotection methods employed here were unable to deprotect commercially available dABz.

| | |
|---|---|
| 5'-$d(T_{10}×T_4)$ SEQ ID NO: 1 | 17 |
| 5'-$d$(TTT AGG CGT GGT GAT GCT GTG TGC TAT GGT) SEQ ID NO: 2 | 18 |
| 5'-$d$(GCT GAT GCG X) SEQ ID NO: 3 | 19 |
| 5'-$d$(CGC AXC GCT GCG) SEQ ID NO: 4 | 20 |
| 5'-$d$(GTG CXT GTT TGT) SEQ ID NO: 5 | 21 |
| 5'-$d$(AAC CXG AGG CCC) SEQ ID NO: 6 | 22 |
| 5'-$d$(AAC CGG AXG CCC) SEQ ID NO: 7 | 23 |
| 5'-$d$(GGA AGC AAT XGT ACG G) SEQ ID NO: 8 | 24 |
| 5'-$d$(CCG ACX TCG CAT CAG C) SEQ ID NO: 13 | 25 |
| 5'-$d$(AGG GCG GTG TXG GAA GAG GGA) SEQ ID NO: 9 | 26 |
| 5'-$d$(AAC CXG AGG CCC ATC CTC AC) SEQ ID NO: 10 | 27 |
| 5'-$d$(GTG CXT GTT TGT GCC TGT CC) SEQ ID NO: 11 | 28 |
| 5'-$d$(TGT TCA TCA TGG GTC XTC GGT ATA TCC CAT) SEQ ID NO: 12 | 29 | x=Fapy·Dg.

A=adenosine; C=Cytidine; G=Guanosine; T=Thymidine

4. Summary

Fapy·dG is a biologically interesting DNA lesion formed from a common intermediate as the most well studied DNA lesion, 8-OxodGuo. Moreover, Fapy·dG is formed in greater quantities than the latter under some $O_2$ deficient conditions. Structural and biochemical knowledge of Fapy·dG, as well as its effects on replication and transcription in cells, is limited due to difficulties in synthesizing oligonucleotides containing it. Consequently, research on the formamidopyrimidines has lagged behind that of 8-OxodGuo. The presently disclosed subject matter discloses the implementation of a synthetic strategy using reverse phosphoramidites that is a marked improvement over previously reported methods for synthesizing oligonucleotides containing Fapy·dG. The process is robust enabling the synthesis of oligonucleotides containing Fapy·dG suitable for biochemical and structural studies. The presently disclosed approach also should be compatible with synthesizing oligonucleotides containing N5-alkylated formamidopyrimidines. The synthesis of phosphoramidite 1, and its compatibility with readily available solid-phase oligonucleotide synthesis reagents will facilitate research on this biologically significant family of DNA lesions.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Cadet, J., Davies, K. J. A., Medeiros, M. H. G., Di Mascio, P. and Wagner, J. R. (2017) Formation and repair of oxidatively generated damage in cellular DNA. *Free Rad. Biol. Med.*, 107, 13-34.

Dizdaroglu, M. (2015) Oxidatively induced DNA damage and its repair in cancer. *Mutat. Res. Rev. Mutagen.*, 763, 212-245.

Fleming, A. M., Ding, Y. and Burrows, C. J. (2017) Oxidative DNA damage is epigenetic by regulating gene transcription via base excision repair. *Proc. Natl. Acad. Sci. USA*, 114, 2604-2609.

Redstone, S. C. J., Fleming, A. M. and Burrows, C. J. (2019) Oxidative Modification of the Potential G-Quadruplex Sequence in the PCNA Gene Promoter Can Turn on Transcription. *Chem. Res. Toxicol.*, 32, 437-446.

Zhu, J., Fleming, A. M. and Burrows, C. J. (2018) The RAD17 Promoter Sequence Contains a Potential Tail-Dependent G-Quadruplex That Downregulates Gene Expression upon Oxidative Modification. *ACS Chem. Biol.*, 13, 2577-2584.

Pan, L., Zhu, B., Hao, W., Zeng, X., Vlahopoulos, S. A., Hazra, T. K., Hegde, M. L., Radak, Z., Bacsi, A., Brasier, A. R. et al. (2016) Oxidized Guanine Base Lesions Function in 8-Oxoguanine DNA Glycosylase-1-mediated Epigenetic Regulation of Nuclear Factor KB-driven Gene Expression. *J. Biol. Chem.*, 291, 25553-25566.

Allgayer, J., Kitsera, N., Bartelt, S., Epe, B. and Khobta, A. (2016) Widespread transcriptional gene inactivation initiated by a repair intermediate of 8-oxoguanine. *Nucleic Acids Res.*, 44, 7267-7280.

Shafirovich, V. and Geacintov, N. E. (2017) Removal of oxidatively generated DNA damage by overlapping repair pathways. *Free Rad. Biol. Med.*, 107, 53-61.

Amente, S., Di Palo, G., Scala, G., Castrignano, T., Gorini, F., Cocozza, S., Moresano, A., Pucci, P., Ma, B., Stepanov, I. et al. (2019) Genome-wide mapping of 8-oxo-7,8-dihydro-2'-deoxyguanosine reveals accumulation of oxidatively-generated damage at DNA replication origins within transcribed long genes of mammalian cells. *Nucleic Acids Res.*, 47, 221-236.

Freudenthal, B. D., Beard, W. A., Perera, L., Shock, D. D., Kim, T., Schlick, T. and Wilson, S. H. (2015) Uncovering the polymerase-induced cytotoxicity of an oxidized nucleotide. *Nature*, 517, 635-639.

Menoni, H., Shukla, M. S., Gerson, V. r., Dimitrov, S. and Angelov, D. (2012) Base excision repair of 8-oxoG in dinucleosomes. *Nucleic Acids Res.*, 40, 692-700.

van der Kemp, P. A., de Padula, M., Burguiere-Slezak, G., Ulrich, H. D. and Boiteux, S. (2009) PCNA monoubiquitylation and DNA polymerase {eta} ubiquitin-binding domain are required to prevent 8-oxoguanine-induced mutagenesis in *Saccharomyces cerevisiae*. *Nucleic Acids Res.*, 37, 2549-2559.

McCulloch, S. D., Kokoska, R. J., Garg, P., Burgers, P. M. and Kunkel, T. A. (2009) The efficiency and fidelity of 8-oxo-guanine bypass by DNA polymerases {delta} and {eta}. *Nucleic Acids Res.*, 37, 2830-2840.

Greenberg, M. M. (2012) The Formamidopyrimidines: Purine Lesions Formed in Competition With 8-Oxopurines From Oxidative Stress. *Acc. Chem. Res.*, 45, 588-597.

Becker, S., Thoma, I., Deutsch, A., Gehrke, T., Mayer, P., Zipse, H. and Carell, T. (2016) A high-yielding, strictly regioselective prebiotic purine nucleoside formation pathway. *Science*, 352, 833-836.

Dizdaroglu, M., Kirkali, G. and Jaruga, P. (2008) Formamidopyrimidines in DNA: Mechanisms of Formation, Repair, and Biological Effects. *Free Rad. Biol. Med.*, 45, 1610-1621.

Jaruga, P., Kirkali, G. and Dizdaroglu, M. (2008) Measurement of Formamidopyrimidines in DNA. *Free Rad. Biol. Med.*, 45, 1601-1609.

Douki, T., Martini, R., Ravanat, J.-L., Turesky, R. J. and Cadet, J. (1997) Measurement of 2,6-Diamino-4-hydroxy-5-formamidopyrimidine and 8-Oxo-7,8-dihydroguanine in Isolated DNA Exposed to Gamma Radiation in Aqueous Solution. *Carcinogenesis*, 18, 2385-2391.

Pouget, J. P., Frelon, S., Ravanat, J. L., Testard, I., Odin, F. and Cadet, J. (2002) Formation of Modified DNA Bases in Cells Exposed either to Gamma Radiation or to High-LET Particles. *Radiat. Res.*, 157, 589-595.

Cadet, J. and Wagner, J. R. (2013) DNA base damage by reactive oxygen species, oxidizing agents, and UV radiation. *Cold Spring Harbor Perspect. Biol.*, 5, A012559/012551-A012559/012518.

Xue, L. and Greenberg, M. M. (2007) Facile Quantification of Lesions Derived From 2'-Deoxyguanosine in DNA. *J. Am. Chem. Soc.*, 129, 7010-7011.

Alshykhly, O. R., Fleming, A. M. and Burrows, C. J. (2015) 5-Carboxamido-5-formamido-2-iminohydantoin, in Addition to 8-oxo-7,8-Dihydroguanine, Is the Major Product of the Iron-Fenton or X-ray Radiation-Induced Oxidation of Guanine under Aerobic Reducing Conditions in Nucleoside and DNA Contexts. *J. Org. Chem.*, 80, 6996-7007.

Douki, T., Riviere, J. and Cadet, J. (2002) DNA Tandem Lesions Containing 8-Oxo-7,8-dihydroguanine and Formamido Residues Arise from Intramolecular Addition of Thymine Peroxyl Radical to Guanine. *Chem. Res. Toxicol.*, 15, 445-454.

Bergeron, F., Auvre, F., Radicella, J. P. and Ravanat, J.-L. (2010) HO. radicals induce an unexpected high proportion of tandem lesion base lesions refractory to repair by DNA glycosylases. *Proc. Nat. Acad. Sci. USA,* 107, 5528-5533.

Wiederholt, C. J., Delaney, M. O., Pope, M. A., David, S. S. and Greenberg, M. M. (2003) Repair of DNA Containing Fapy·dG and Its β-C-Nucleoside Analogue by Formamidopyrimidine DNA Glycosylase and Mut Y. *Biochemistry,* 42, 9755-9760.

Krishnamurthy, N., Haraguchi, K., Greenberg, M. M. and David, S. S. (2008) Efficient Removal of Formamidopyrimidines by 8-Oxoguanine Glycosylases. *Biochemistry,* 47, 1043-1050.

Chmiel, N. H., Livingston, A. L. and David, S. S. (2003) Insight into the Functional Consequences of Inherited Variants of the hMYH Adenine Glycosylase Associated with Colorectal Cancer: Complementation Assays with hMYH Variants and Pre-steady-state Kinetics of the Corresponding Mutated *E. coli* Enzymes. *J. Mol. Biol,* 327, 431-443.

Porello, S. L., Leyes, A. E. and David, S. S. (1998) Single-Turnover and Pre-Steady-State Kinetics of the Reaction of the Adenine Glycosylase MutY with Mismatch-Containing DNA Substrates. *Biochemistry,* 37, 14756-14764.

Patro, J. N., Wiederholt, C. J., Jiang, Y. L., Delaney, J. C., Essigmann, J. M. and Greenberg, M. M. (2007) Studies on the Replication of the Ring Opened Formamidopyrimidine, Fapy·dG in *Escherichia coli. Biochemistry,* 46, 10202-10212.

Kalam, M. A., Haraguchi, K., Chandani, S., Loechler, E. L., Moriya, M., Greenberg, M. M. and Basu, A. K. (2006) Genetic Effects of Oxidative DNA Damages: Comparative Mutagenesis of the Imidazole Ring-Opened Formamidopyrimidines (Fapy Lesions) and 8-Oxo-purines in Simian Kidney Cells. *Nucleic Acids Res.,* 34, 2305-2315.

Pande, P., Haraguchi, K., Jiang, Y.-L., Greenberg, M. M. and Basu, A. K. (2015) Unlike Catalyzing Error-Free Bypass of 8-OxodGuo, DNA Polymerase λ Is Responsible for a Significant Part of Fapy·dG-Induced G→T Mutations in Human Cells. *Biochemistry,* 54, 1859-1862.

Gehrke, T. H., Lischke, U., Gasteiger, K. L., Schneider, S., Arnold, S., Müller, H. C., Stephenson, D. S., Zipse, H. and Carell, T. (2013) Unexpected non-Hoogsteen, Aìbased mutagenicity mechanism of FaPy-DNA lesions. *Nature Chem. Biol.,* 9, 455-461. Coste, F., Ober, M., Carell, T., Boiteux, S., Zelwer, C. and Castaing, B. (2004) Structural Basis for the Recognition of the FapydG Lesion (2,6-Diamino-4-hydroxy-5-formamidopyrimidine) by Formamidopyrimidine-DNA Glycosylase. *J. Biol. Chem.,* 279, 44074-44083.

Berger, M. and Cadet, J. (1985) Isolation and Characterization of the Radiation-Induced Degradation Products of 2'-Deoxyguanosine in Oxygen-Free Solutions. *Z. Naturforsch.,* 40b, 1519-1531.

Patro, J. N., Haraguchi, K., Delaney, M. O. and Greenberg, M. M. (2004) Probing the Configurations of Formamidopyrimidine Lesions Fapy·dA and Fapy·dG in DNA Using Endonuclease IV. *Biochemistry,* 43, 13397-13403.

Burgdorf, L. T. and Carell, T. (2002) Synthesis, Stability, and Conformation of the Formamidopyrimidine G DNA Lesion. *Chem. Eur. J.,* 8, 293-301.

Delaney, M. O. and Greenberg, M. M. (2002) Synthesis of Oligonucleotides and Thermal Stability of Duplexes Containing the f3-C-Nucleotide Analogue of Fapy·dG. *Chem. Res Toxicol.,* 15, 1460-1465.

Christov, P. P., Brown, K. L., Kozekov, I. D., Stone, M. P., Harris, T. M. and Rizzo, C. J. (2008) Site-Specific Synthesis and Characterization of Oligonucleotides Containing an N6-(2-Deoxy-derythro-pentofuranosyl)-2,6-diamino-3,4-dihydro-4-oxo-5-N-methylformamidopyrimidine Lesion, the Ring-Opened Product from N7-Methylation of Deoxyguanosine. *Chem. Res. Toxicol.,* 21, 2324-2333.

Christov, P. P., Angel, K. C., Guengerich, F. P. and Rizzo, C. J. (2009) Replication Past the N5-methyl-formamidopyrimidine Lesion of Deoxyguanosine by DNA Polymerases and an Improved Procedure for Sequence Analysis of in vitro Bypass Products by Mass Spectrometry. *Chem. Res. Toxicol.,* 22, 1086-1095.

Lukin, M., Minetti, C. A. S. A., Remeta, D. P., Attaluri, S., Johnson, F., Breslauer, K. J. and de los Santos, C. (2011) Novel post-synthetic generation, isomeric resolution, and characterization of Fapy-dG within oligodeoxynucleotides: differential anomeric impacts on DNA duplex properties. *Nucleic Acids Res.,* 39, 5776-5789.

Haraguchi, K., Delaney, M. O., Wiederholt, C. J., Sambandam, A., Hantosi, Z. and Greenberg, M. M. (2002) Synthesis and Characterization of Oligodeoxynucleotides Containing Formamidopyrimidine Lesions and Nonhydrolyzable Analogues. *J. Am. Chem. Soc.,* 124, 3263-3269.

Haraguchi, K. and Greenberg, M. M. (2001) Synthesis of Oligonucleotides Containing Fapy·dG (N6-(2-Deoxy-α,β-D-erythro-pento-furanosyl)-2,6-diamino-4-hydroxy-5-formamidopyrimidine). *J. Am. Chem. Soc.,* 123, 8636-8637.

Jiang, Y. L., Wiederholt, C. J., Patro, J. N., Haraguchi, K. and Greenberg, M. M. (2005) Synthesis of Oligonucleotides Containing Fapy·dG (N-(2-Deoxy-α,β-D-erythropentofuranosyl)-N-(2,6-diamino-4-hydroxy-5-formamidopyrimidine)) Using a 5'-Dimethoxytrityl Dinucleotide Phosphoramidite. *J. Org. Chem.,* 70, 141-147.

Bag, S. S., Talukdar, S., Matsumoto, K. and Kundu, R. (2013) Triazolyl Donor/Acceptor Chromophore Decorated Unnatural Nucleosides and Oligonucleotides with Duplex Stability Comparable to That of a Natural Adenine/Thymine *J. Org. Chem.,* 78, 278-291.

Rolland, V., Kotera, M. and Lhomme, J. (1997) Convenient Preparation of 2-Deoxy-3,5-di-Op-toluoyl-α-D-erythro-pentofuranosyl Chloride. *Syn. Comm.,* 27, 3505-3511.

Robins, M. J., Zou, R., Guo, Z. and Wnuk, S. F. (1996) Nucleic Acid Related Compounds. 93. A Solution for the Historic Problem of Regioselective Sugar-Base Coupling To Produce 9-Glycosylguanines or 7-Glycosylguanines. *J. Org. Chem.,* 61, 9207-9212.

Kamimura, T., Tsuchiya, M., Urakami, K., Koura, K., Sekine, M., Shinozaki, K., Miura, K. and Hata, K. (1984) Synthesis of a dodecaribonucleotide, GUAUCAAUAAUG, by use of "fully" protected ribonucleotide building blocks. *J. Am. Chem. Soc.,* 106, 4552-4557.

Cai, H. and Guengerich, F. P. (2000) Acylation of Protein Lysines by Trichloroethylene Oxide. *Chem. Res. Toxicol.,* 13, 327-335.

Pratap, T. V. and Baskaran, S. (2001) Direct conversion of aryl nitro compounds to formanilides under catalytic transfer hydrogenation conditions. *Tetrahedron Lett.,* 42, 1983-1985.

Schijf, R. and Stevens, W. (1966) Mixed carboxylic acid anhydrides VII. Synthesis of some mixed formic acid anhydrides. *Recl. Trav. Chim. Pays-Bas,* 85, 627-628.

Vlietstra, E. J., Zwikker, J. W., Nolte, R. J. M. and Drenth, W. (1982) Trimethylacetic formic anhydride. Improved preparation and use as a highly efficient and selective N-formylating reagent. *Recl. Trav. Chim. Pays-Bas,* 101, 460-461.

Scaringe, S. A., Wincott, F. E. and Caruthers, M. H. (1998) Novel RNA Synthesis Method Using 5'-O-Silyl-2'-O-orthoester Protecting Groups. *J. Am. Chem. Soc.,* 120, 11820-11821.

Reddy, M. P., Hanna, N. B. and Farooqui, F. (1994) Fast cleavage and deprotection of oligonucleotides. *Tetrahedron Lett.,* 35, 4311-4314.

*The Glen Report* (2013) In Research, G. (ed.), Sterling, Va. 20164.

Babaoglu, K. Qi, J. Lee, R. E. and White S. W. (2004) Crystal Structure of 7,8-Dihydropteroate Synthase from *Bacillus anthracis*: Mechanism and Novel Inhibitor Design. Structure 12, 1705-1717.

Ravikumar, V. T., Kumar, R. K., Olsen, P., Moore, M. N., Carty, R. L., Andrade, M., Gorman, D., Zhu, X., Cedillo, I., Wang, Z., Mendez, L., Scozzari, A. N., Aguirre, G., Somanathan, R., and Berneès, UnyLinker: An Efficient and Scaleable Synthesis of Oligonucleotides Utilizing a Universal Linker Molecule: A Novel Approach To Enhance the Purity of Drugs, *Org. Process Res. Dev.* 2008, 12, 3, 399-410.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for synthesizing an oligonucleotide, the method comprising:
   (a) providing a nucleoside phosphoramidite comprising a 2'-deoxyribose moiety having a 3'-hydroxyl position and a 5'-hydroxyl position, wherein the nucleoside phosphoramidite has a dimethoxytrityl protecting group at the 3'-hydroxyl position and a phosphoramidite moiety at the 5'-hydroxyl position, wherein the nucleoside phosphoramidite has the following structure:

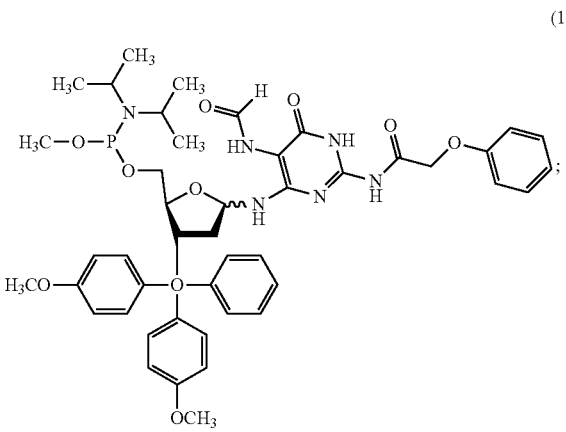

(1)

and
   (b) contacting the nucleoside phosphoramidite of (a) with one or more nucleoside residues attached to a solid phase support to form a solid support-bound product.

2. The method of claim 1, wherein the solid phase support comprises one or more of a universal support, one or more nucleoside or nucleoside analogues, and one or more nucleoside residues attached to the solid phase support comprise one or more thymidines and a single Fapy·dG moiety on a reverse 3'-thymidine support comprising a succinate linkage between the 5'-hydroxyl group and a long chain alkylamine linker to the solid phase support:

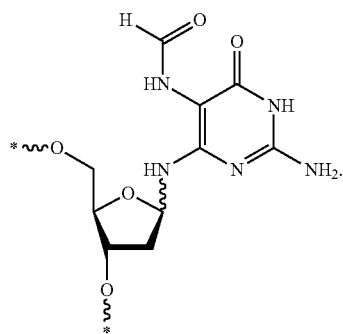 [SMILES: *OC[C@H]1O[C@@H](Nc2nc(N)[nH]c(=O)c2NC=O)C[C@H]1O*]

3. The method of claim 1, further comprising detritylating the nucleoside phosphoramidite having a dimethoxytrityl protecting group at the 3'-hydroxyl position.

4. The method of claim 3, comprising contacting the nucleoside phosphoramidite having a dimethoxytrityl protecting group at the 3'-hydroxyl position with trichloroacetic acid (TCA) or dichloroacetic acid (DCA).

5. The method of claim 3, further comprising removing a dimethoxytrityl cation formed during the detritylation of the nucleoside phosphoramidite having a dimethoxytrityl protecting group at the 3'-hydroxyl position.

6. The method of claim 1, further comprising contacting the nucleoside phosphoramidite of (a) with an activator before contacting it with the one or more nucleoside residues attached to a solid phase support.

7. The method of claim 6, wherein the activator is selected from the group consisting of 4,5-dicyanoimidazole, 1H-tetrazole, 5-ethylthio-1H-tetrazole, 2-benzylthiotetrazole, 5-(p-nitrophenyl)-1H-tetrazole, and benzimidazolium triflate.

8. The method of claim 1, further comprising contacting the solid support-bound product with an oxidizing agent to form an oxidized solid support-bound product.

9. The method of claim 8, wherein the oxidizing agent is selected from the group consisting of tert-butyl hydroperoxide (t-BuOOH), $I_2$/water, and (1S)-(+)-(10-camphorsulfonyl)-oxaziridine (CSO).

10. The method of claim 8, wherein the oxidized product comprises a phosphate triester.

11. The method of claim 1, further comprising capping the solid support-bound product of (b).

12. The method of claim 11, comprising contacting treating the solid support-bound product with a solution comprising pivalic anhydride/lutidine/tetrahydrofuran (THF).

13. The method of claim 10, further comprising demethylating the phosphate triester.

14. The method of claim 13, wherein the demethylating of the phosphate triester comprises contacting the phosphate triester with disodium 2-carbamoyl-2-cyanoethylene-1,1-dithiolate trihydrate.

15. The method of claim 1, further comprising deprotecting and/or cleaving the solid support-bound product of (b).

16. The method of claim 15, comprising contacting the solid support-bound product of (b) with one or more of aqueous ammonia, NaOH, $K_2CO_3$, t-butylamine, and combinations thereof.

17. The method of claim 15, further comprising purifying the deprotected and/or cleaved solid support-bound product of (b).

18. The method of claim 17, comprising purifying the deprotected and/or cleaved solid support-bound product of (b) with gel electrophoresis or reversed phase high performance liquid chromatography (HPLC).

19. The method of claim 1, wherein the one or more nucleoside residues attached to the solid phase support comprise at least one N6-(2-Deoxy-α,β-D-erythropentofuranosyl)-2,6-diamino-4-hydroxy-5-formamidopyrimidine (Fapy·dG) moiety:

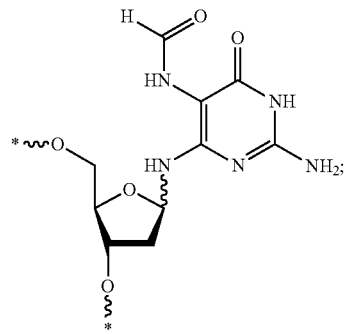 [SMILES: *OC[C@H]1O[C@@H](Nc2nc(N)[nH]c(=O)c2NC=O)C[C@H]1O*]

wherein * denotes a point of attachment of the Fapy·dG moiety to one or more other nucleosides.

20. The method of claim 1, wherein the one or more nucleoside residues attached to the solid phase support comprise at least one N4-(2-Deoxy-α,β-D-erythropentofuranosyl)-4,6-diamino-5-formamidopyrimidine (Fapy·dA) moiety:

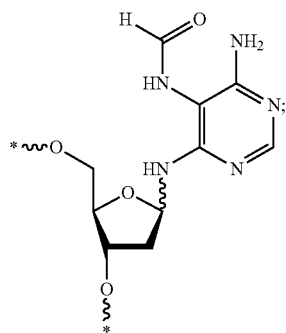 [SMILES: *OC[C@H]1O[C@@H](Nc2ncnc(N)c2NC=O)C[C@H]1O*]

wherein * denotes a point of attachment of the Fapy·dA moiety to one or more other nucleosides.

21. The method of claim 1, wherein the synthesized oligonucleotide comprises at least one Fapy·dG moiety and/or at least one Fapy·dA moiety.

22. The method of claim 1, wherein the synthesized oligonucleotide comprises one or more nucleoside selected from the group consisting of adenosine (A), guanosine (G), cytidine (C), and thymidine (T).

23. The method of claim 1, wherein the method comprises:
(a) providing a nucleoside phosphoramidite comprising a 2'-deoxyribose moiety having a 3'-hydroxyl position and a 5'-hydroxyl position, wherein the nucleoside phosphoramidite has a dimethoxytrityl protecting group at the 3'-hydroxyl position and a phosphoramidite moiety at the 5'-hydroxyl position;
(b) detritylating the nucleoside phosphoramidite having a dimethoxytrityl protecting group at the 3'-hydroxyl position of (a) to form a detritylated nucleoside phosphoramidite;
(c) contacting the detritylated nucleoside phosphoramidite of (b) with an activator to form an activated detritylated nucleoside phosphoramidite;
(d) contacting the activated detritylated nucleoside phosphoramidite of (c) with one or more nucleoside residues attached to a solid phase support to form a solid support-bound product;
(e) contacting the solid support-bound product of (d) with an oxidizing agent to form an oxidized solid support-bound product;
(f) capping the oxidized solid support-bound product of (e) to form a capped solid support-bound product; and
(g) deprotecting and/or cleaving the capped solid support-bound product of (f).

24. A method for synthesizing an oligonucleotide, the method comprising:
(a) providing a nucleoside phosphoramidite comprising a 2'-deoxyribose moiety having a 3'-hydroxyl position and a 5'-hydroxyl position, wherein the nucleoside phosphoramidite has a dimethoxytrityl protecting group at the 3'-hydroxyl position and a phosphoramidite moiety at the 5'-hydroxyl position, wherein the nucleoside phosphoramidite has the following structure:

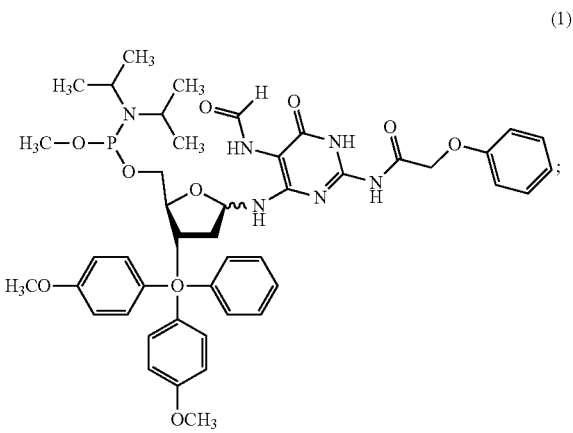

and
(b) contacting the nucleoside phosphoramidite of (a) with one or more nucleoside residues attached to a solid phase support to form a solid support-bound product, wherein the synthesized oligonucleotide is selected from the group consisting of:

| | |
|---|---|
| 5'-d($T_{10}$×$T_4$) SEQ ID NO: 1 | 17 |
| 5'-d(TTT AGG CGT GGT GAT GCT GTG TGC TAT GGT) SEQ ID NO: 2 | 18 |
| 5'-d(GCT GAT GCG X) SEQ ID NO: 3 | 19 |
| 5'-d(CGC AXC GCT GCG) SEQ ID NO: 4 | 20 |
| 5'-d(GTG CXT GTT TGT) SEQ ID NO: 5 | 21 |
| 5'-d(AAC CXG AGG CCC) SEQ ID NO: 6 | 22 |
| 5'-d(AAC CGG AXG CCC) SEQ ID NO: 7 | 23 |
| 5'-d(GGA AGC AAT XGT ACG G) SEQ ID NO: 8 | 24 |
| 5'-d(CCG ACX TCG CAT CAG C) SEQ ID NO: 13 | 25 |
| 5'-d(AGG GCG GTG TXG GAA GAG GGA) SEQ ID NO: 9 | 26 |
| 5'-d(AAC CXG AGG CCC ATC CTC AC) SEQ ID NO: 10 | 27 |
| 5'-d(GTG CXT GTT TGT GCC TGT CC) SEQ ID NO: 11 | 28 |
| 5'-d(TGT TCA TCA TGG GTC XTC GGT ATA TCC CAT) SEQ ID NO: 12 | 29 | x=Fapy·dG.

* * * * *